US011382516B2

(12) United States Patent
Wu et al.

(10) Patent No.: US 11,382,516 B2
(45) Date of Patent: Jul. 12, 2022

(54) APPARATUSES, METHODS, AND STORAGE MEDIUMS FOR LUMEN AND ARTIFACTS DETECTION IN ONE OR MORE IMAGES, SUCH AS IN OPTICAL COHERENCE TOMOGRAPHY IMAGES

(71) Applicant: CANON U.S.A., INC., Melville, NY (US)

(72) Inventors: Bin Wu, West Roxbury, MA (US); Tzu-Yu Wu, Malden, MA (US)

(73) Assignee: Canon U.S.A., Inc., Melville, NY (US)

( * ) Notice: Subject to any disclaimer, the term of this patent is extended or adjusted under 35 U.S.C. 154(b) by 558 days.

(21) Appl. No.: 16/414,222

(22) Filed: May 16, 2019

(65) Prior Publication Data

US 2019/0374109 A1    Dec. 12, 2019

Related U.S. Application Data

(60) Provisional application No. 62/682,598, filed on Jun. 8, 2018.

(51) Int. Cl.
   *G06T 7/13* (2017.01)
   *G06T 5/00* (2006.01)
   (Continued)

(52) U.S. Cl.
   CPC .......... *A61B 5/0084* (2013.01); *A61B 5/0066* (2013.01); *A61B 5/7203* (2013.01);
   (Continued)

(58) Field of Classification Search
   None
   See application file for complete search history.

(56) References Cited

U.S. PATENT DOCUMENTS

| 5,357,550 A | 10/1994 | Asahina et al. |
| 6,565,514 B2 | 5/2003 | Svanerudh et al. |

(Continued)

FOREIGN PATENT DOCUMENTS

| EP | 3831279 A1 * | 6/2021 | ........... A61B 5/0066 |
| JP | 2007-101249 A | 4/2007 | |

(Continued)

OTHER PUBLICATIONS

Nam et al. "Automated detection of vessel lumen and stent struts in intravascular optical coherence tomography to evaluate stent apposition and neointimal coverage", Med. Phys. 43 (4), Apr. 2016 (Year: 2016).*

(Continued)

*Primary Examiner* — Randolph I Chu
(74) *Attorney, Agent, or Firm* — Canon U.S.A., Inc. I.P. Division

(57) ABSTRACT

One or more devices, systems, methods and storage mediums for performing optical coherence tomography (OCT) while detecting one or more lumen edges and/or one or more artifacts are provided. Examples of applications include imaging, evaluating and diagnosing biological objects, such as, but not limited to, for Gastro-intestinal, cardio and/or ophthalmic applications, and being obtained via one or more optical instruments, such as, but not limited to, optical probes, catheters, capsules and needles (e.g., a biopsy needle). Preferably, the OCT devices, systems methods and storage mediums include or involve a method, such as, but not limited to, for removing the detected one or more artifacts from the image(s).

21 Claims, 18 Drawing Sheets

(51) Int. Cl.
*A61B 5/00* (2006.01)
*A61B 8/12* (2006.01)
*A61B 8/08* (2006.01)
*G06T 11/00* (2006.01)
*G06T 5/20* (2006.01)

(52) U.S. Cl.
CPC ............... *A61B 5/725* (2013.01); *A61B 8/12* (2013.01); *A61B 8/5269* (2013.01); *G06T 5/002* (2013.01); *G06T 5/20* (2013.01); *G06T 7/13* (2017.01); *G06T 11/008* (2013.01); *G06T 2207/10101* (2013.01); *G06T 2207/10132* (2013.01); *G06T 2207/20024* (2013.01); *G06T 2207/20182* (2013.01)

(56) References Cited

U.S. PATENT DOCUMENTS

| | | | |
|---|---|---|---|
| 6,763,261 | B2 | 7/2004 | Casscells, III et al. |
| 7,366,376 | B2 | 4/2008 | Shishkov et al. |
| 7,414,779 | B2 | 8/2008 | Huber et al. |
| 7,843,572 | B2 | 11/2010 | Tearney et al. |
| 7,872,759 | B2 | 1/2011 | Tearney et al. |
| 7,889,348 | B2 | 2/2011 | Tearney et al. |
| 7,916,387 | B2 | 3/2011 | Schmitt |
| 7,978,916 | B2 | 7/2011 | Klingensemith et al. |
| 8,289,522 | B2 | 10/2012 | Tearney et al. |
| 8,315,282 | B2 | 11/2012 | Huber et al. |
| 8,325,419 | B2 | 12/2012 | Schmitt |
| 8,412,312 | B2 | 4/2013 | Judell et al. |
| 8,478,387 | B2 | 7/2013 | Xu |
| 8,493,567 | B2 | 7/2013 | Inoue |
| 8,581,643 | B1 | 11/2013 | Schmitt |
| 8,831,321 | B1 | 9/2014 | Elbasiony |
| 8,909,323 | B2 | 12/2014 | Baumgart |
| 8,913,084 | B2 | 12/2014 | Chen et al. |
| 8,928,889 | B2 | 1/2015 | Tearney et al. |
| RE45,534 | E | 6/2015 | Huennekens et al. |
| 9,087,368 | B2 | 7/2015 | Tearney et al. |
| 9,121,926 | B2 | 9/2015 | Nair et al. |
| 9,138,147 | B2 | 9/2015 | Schmitt et al. |
| 9,173,591 | B2 | 11/2015 | Elbasiony et al. |
| 9,207,064 | B2 | 12/2015 | Inoue |
| 9,286,673 | B2 | 3/2016 | Begin et al. |
| 9,292,918 | B2 | 3/2016 | Zagrodsky et al. |
| 9,295,450 | B2 | 3/2016 | Furuichi et al. |
| 9,301,687 | B2 | 4/2016 | Kemp |
| 9,307,926 | B2 | 4/2016 | Begin et al. |
| 9,324,141 | B2 | 4/2016 | Begin |
| 9,332,942 | B2 | 5/2016 | Jaffer et al. |
| 9,351,698 | B2 | 5/2016 | Dascal et al. |
| 9,355,474 | B2 | 5/2016 | Celi et al. |
| 9,462,950 | B2 | 10/2016 | Xu |
| 9,659,375 | B2 | 5/2017 | Zagrodsky et al. |
| 9,858,668 | B2 | 1/2018 | Jones et al. |
| 2010/0092389 | A1 | 4/2010 | Jaffer et al. |
| 2010/0094127 | A1 | 4/2010 | Xu |
| 2012/0101374 | A1 | 4/2012 | Tearney et al. |
| 2014/0100440 | A1 | 4/2014 | Cheline et al. |
| 2014/0276011 | A1 | 9/2014 | Schmitt et al. |
| 2015/0250438 | A1 | 9/2015 | Bozkaya et al. |
| 2015/0272442 | A1 | 10/2015 | Motafakker-Fard et al. |
| 2016/0171711 | A1 | 6/2016 | Gopinath et al. |
| 2016/0228097 | A1 | 8/2016 | Jaffer et al. |
| 2016/0335766 | A1 | 11/2016 | Ambwani et al. |
| 2017/0020392 | A1 | 1/2017 | Xu |
| 2017/0024532 | A1 | 1/2017 | Gopinath et al. |
| 2017/0309018 | A1 | 10/2017 | Shalev et al. |
| 2018/0003481 | A1 | 1/2018 | Yamada et al. |
| 2018/0045501 | A1 | 2/2018 | Elmaanaoui |

FOREIGN PATENT DOCUMENTS

| | | | | |
|---|---|---|---|---|
| JP | 2010-179043 A | | 8/2010 | |
| JP | 2012-002597 A | | 1/2012 | |
| JP | 2013-66559 A | | 4/2013 | |
| JP | 2015-535723 A | | 12/2015 | |
| JP | 2020018840 A | * | 2/2020 | ........... A61B 5/0066 |
| WO | 2014055923 A2 | | 4/2014 | |
| WO | 2016094909 A1 | | 6/2016 | |

OTHER PUBLICATIONS

Horsley, E., "Imaging for the Future; Intravascular Optical Coherence Tomography", Sep. 10, 2016; from https://www.slideshare.net/ErnestHorsley/coronary-optical-coherence-tomography-oct-angio-coregistration-acr-and-metal-stent-optimisation-mso-softwarefrom (includes 42 pages).

St Jude Web Page "OPTIS Stent Optimization Software" downloaded Feb. 10, 2017: https://www.sjmglobal.com/professionals/resources-and-reimbursement/technical-resources/vascular/intravascular-diagnostics-and-imaging/intravascular-diagnostics-and-imaging-system-ffr-oct/optis-metallic-stent-optimization-software?halert=show&clset-92f57278-460e-4300-b7fe-89e52a04194f%3acadddb93-fcc4-47f2-8ceb-fd88f01ca17f (includes 3 pages).

* cited by examiner

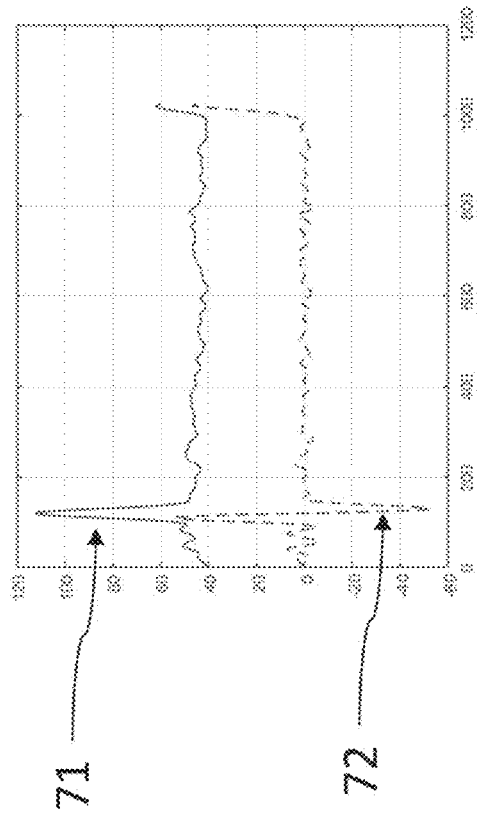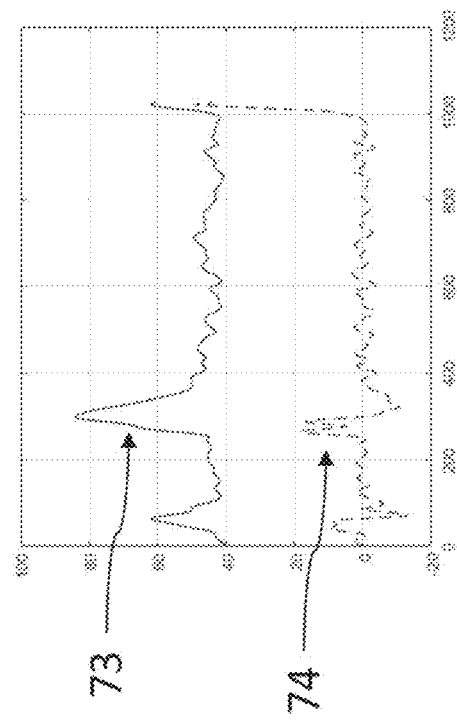
FIG. 7A
FIG. 7B

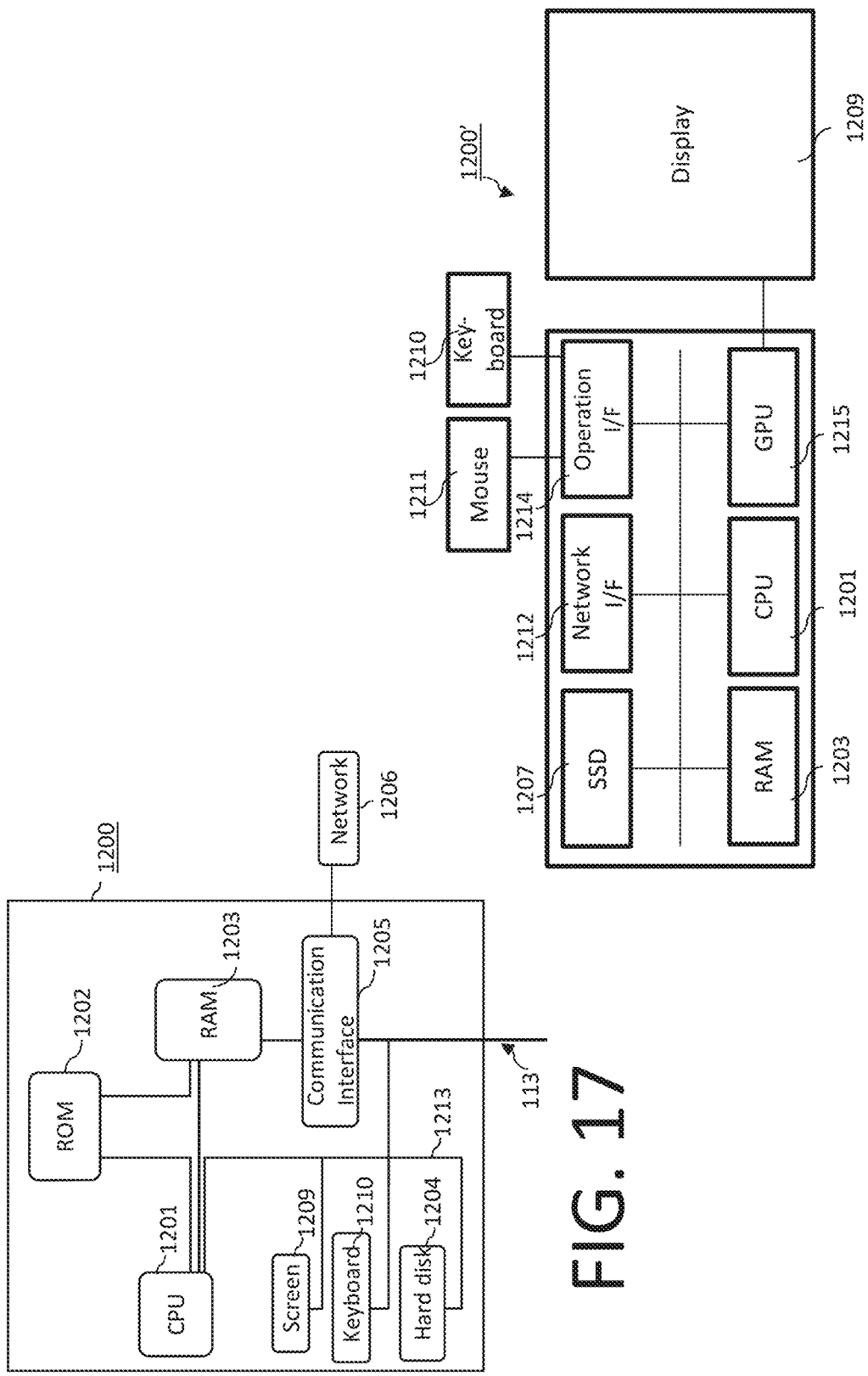

APPARATUSES, METHODS, AND STORAGE MEDIUMS FOR LUMEN AND ARTIFACTS DETECTION IN ONE OR MORE IMAGES, SUCH AS IN OPTICAL COHERENCE TOMOGRAPHY IMAGES

CROSS-REFERENCE TO RELATED APPLICATION(S)

This application relates, and claims priority, to U.S. Prov. Patent Application Ser. No. 62/682,598, filed Jun. 8, 2018, the entire disclosure of which is incorporated by reference herein in its entirety.

FIELD OF THE INVENTION

The present disclosure relates generally to the field of optical imaging and more particularly to one or more optical apparatuses, systems, methods (for using and/or manufacturing) and storage mediums, such as, but not limited to, fiber optic catheters, endoscopes and/or optical coherence tomography (OCT) and/or fluorescence apparatuses and systems, and methods and storage mediums, for use with same, to achieve lumen and artifacts detection of images, such as OCT or other (e.g., intravascular ultrasound (IVUS), other lumen image(s), etc.) images. Examples of such applications include imaging, evaluating and diagnosing biological objects, such as, but not limited to, for cardio and/or ophthalmic applications, and being obtained via one or more optical instruments, such as, but not limited to, optical probes, catheters, endoscopes, phase shift units (e.g., galvanometer scanner) and bench top systems.

BACKGROUND OF THE INVENTION

Fiber optic catheters and endoscopes have been developed to access to internal organs. For example in cardiology, OCT has been developed to see depth resolved images of vessels with a catheter. The catheter, which may include a sheath, a coil and an optical probe, may be navigated to a coronary artery.

Optical coherence tomography (OCT) is a technique for obtaining high resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency.

The frequency of the interference patterns corresponds to the distance between the sample arm and the reference arm. The higher frequencies are, the more the path length differences are. Single mode fibers are commonly used for OCT optical probes, and double clad fibers are also commonly used for fluorescence and/or spectroscopy.

In order to obtain geometric measurements of blood vessels from OCT images, lumen edges are detected from the OCT images. Often, image processing approaches for lumen edge detection require more or less uniform illumination of the images such that some optimal global threshold(s) can be determined in order for the image processing algorithms to perform lumen edge detection reliably. To further improve the accuracy of the detected lumen edges, the lumen edge detection results from the neighboring OCT images are correlated to remove outliers and smooth the entire lumen edge.

However, the optimality of global threshold(s) for an image is based on certain assumptions of the underlying image pixel intensity distribution, and images do not always satisfy such assumptions. Therefore, the threshold(s) obtained from the image processing algorithms may not be optimal.

Given the varying curvature and size of the blood vessels, OCT images often display non-uniform illuminations. As such, finding the optimal global threshold(s) tends to be impossible or improbable in image processing algorithms involving pixel intensity and/or gradient based edge detection. Therefore, detection results are unreliable using such image processing approaches.

Accordingly, it would be desirable to provide one or more OCT techniques for use in at least one optical device, assembly or system to achieve consistent, reliable detection results at high efficiency and a reasonable cost of manufacture and maintenance.

SUMMARY OF THE INVENTION

Lumen edge detection in OCT imaging may be susceptible to artifacts, which correspond to many features, including, but not limited to: stent strut(s), guide wire(s), image brightness variation due to imaging angle, sheath reflections, an irregular shape of a vessel cross section, etc. Certain applications of OCT, such as multimodality OCT (MMOCT) systems/apparatuses, may use lumen edge detection to correct near-infrared autofluorescence (NIRAF) signal distance attenuation. Preferably, accurate, real-time NIRAF imaging uses accurate detection of lumen edge(s) in real-time based on a single frame of an OCT image. Accurately detecting a lumen edge(s) using a single OCT frame helps to improve overall object or target, such as a vessel, measurement accuracy, including for post processing.

In one or more embodiments of the present disclosure, an OCT image is formed in a polar coordinate domain from A-lines in one or more embodiments. Each A-line includes much information about the imaged object, such as, but not limited to: clear indications of artifacts from metal objects (e.g., stents, stent struts, guide wires, etc.) like narrow signal width and/or sharp rising and falling edges; significant difference in signal intensity and shape for unobstructed soft tissue compared to the sheath reflection and other artifacts like wide signal width and a gentle falling edge. Each A-line represents a cross-sectional 1D sampling of a target, sample, object, etc., such as, but not limited to, a vessel, along a certain view angle. As an imaging probe or device rotates (e.g., rotates about 0 to about 360 degrees, about 180 degrees to about 360 degrees, about 360 degrees, etc.), the corresponding A-lines form the complete 2D cross-section of the target, sample, object, etc. (e.g., the vessel) in polar coordinates, which is then converted into Cartesian coordinates to form the tomographical-view (tomo-view) image of the cross-section of the target, sample, object, etc. (e.g., the vessel).

In one or more embodiments, individual A-lines may be processed to determine the most significant signal source. A one dimensional (1D) edge location may be determined from each A-line. The types of signal source using the significant difference in an A-line may be determined. Edge points from artifacts may be removed, and gaps may be interpolated. A two dimensional (2D) lumen edge may be formed from the 1D edge result(s). As such, one or more embodiments may have improved processing speed because 1D processing may be faster than corresponding 2D processing.

Depending on the vessel curvature, bending, and distance with respect to the imaging probe, some A-lines can have stronger pixel intensity values if the light exiting from imaging probe is close to normal incident to the vessel wall while some other A-lines may have weaker signal when the incidence of the light from the imaging probe to the vessel wall deviates from normal incidence. In addition, when the imaging probe is not located at the center of the vessel, the distance for the light to travel between the probe to the vessel varies as the imaging probe rotates, and produces variation of brightness in one image frame. Therefore the tomo-view of the vessel may display varying pixel intensity from region to region in one image depending on the corresponding imaging angles and imaging distance to the vessel wall.

Given that an OCT image is formed using an imaging probe spinning inside a vessel in one or more embodiments, the significant edge points interested may correspond to the inner wall of the imaged vessel. Such a configuration may limit each tomo-view OCT image as having one fully enclosed lumen edge in one or more embodiments. Such a configuration may translate into a situation where there may be only one pixel of interest (such as, but not limited to one lumen edge pixel of interest, one edge pixel of interest, one pixel of interest, a pixel of interest for an edge that is an edge other than a lumen edge, etc.) in each A-line in one or more embodiments. In one or more embodiments, in the presence of stent struts and guidewires, the lumen edge points of the soft tissue may be fully or partially obstructed. Each A line preferably has only one (1) lumen edge pixel or none (when at least one metal artifact presents) in one or more embodiments.

One or more embodiments of the present disclosure take advantage of this constraint of having only one lumen edge pixel of interest in each A-line in a cross-sectional image in polar coordinate. By utilizing 1D signal processing techniques to determine this single edge pixel in each A-line, one or more embodiments of the present disclosure simplify the lumen edge detection algorithm and completely eliminate the need of finding global optimal thresholds for the cross-sectional 2D image. This allows each A-line to have its own optimal threshold for best detection result (i.e. total number of A-lines corresponds to number of different thresholds in one image).

One or more embodiments of the present disclosure further take advantage of a noticeable A-line shape variation due to artifacts from guidewires and stents, and may introduce the falling and rising gradient ratio (FRGR) as a measure of opaqueness and reflectivity to help identify stents struts and other image artifacts from metal during lumen edge detection.

One or more embodiments of the present disclosure of at least one procedure may be described using at least one flow diagram. The present disclosure describes one or more features of one or more embodiments of methods in detail, including, but not limited to, about how to detect a lumen edge pixel in an A-line, how to identify the edge pixels caused by image artifacts in an OCT image, and how to form the final lumen edge of the imaged vessel.

Accordingly, it is at least one broad object of the present disclosure to provide one or more optical apparatuses, systems, methods (for using and/or manufacturing) and storage mediums, such as, but not limited to, fiber optic catheters, endoscopes and/or optical coherence tomography (OCT) apparatuses and systems, and methods and storage mediums, for use with same, to achieve consistent, reliable detection results, including at a high efficiency, and at a reasonable cost of manufacture and maintenance.

Two image processing approaches for lumen edge detection are: (i) image segmentation based edge detection where optical global or regional threshold(s) are applied to intensity values of pixels of the OCT images to segment the images into different regions before determining the lumen edges from the boundary of the regions; and (ii) gradient based edge detection where some global threshold(s) are applied to the gradient values of the pixels of the image(s) for the entire image(s) and together with the gradient directions to detect the boundaries where there are significant brightness changes around the lumen edges. In one or more embodiments, cross correlation among neighboring images may be used to improve lumen edge detection results. Results may be used for detection of a device, such as a stent. While these approaches may be used in one or more embodiments, other approaches discussed herein provided advantages over the subject two approaches.

One or more additional objects of the present disclosure are to one or more of: (i) avoid using global threshold(s) in a two-dimensional (2D) image in one or more embodiments; and (ii) combine pixel intensity values and the separated gradient along A-line values and gradient across the A-lines values together for edge detection to improve lumen edge detection accuracy in one or more embodiments. For example, in one or more embodiments of avoiding the use of global threshold(s), 2D image processing may be decoupled into separated 1D signal processing, and an adaptive threshold may be used for each one dimensional (1D) signal (i.e., A-line) of the image in polar coordinate(s) for lumen edge detection.

In one or more embodiments, a one dimensional A-line signal reveals more information about the underlying signal. Lumen edge pixel and artifact pixels may be easily identified using the A-line signal. Preferably, in one or more embodiments, each one dimensional data (A-line) has its own optimal threshold for lumen edge detection. Such feature(s) remove(s) the need of finding global optimal threshold(s) in a 2D image, and reduces the computation complexity. One or more of the subject features also reduce(s) the algorithm sensitivity to regional image intensity variation, and/or provides immunity to intensity variation due to the imaging angle and distance changes.

In one or more embodiments, an optical coherence tomography system for detecting one or more lumen edges and one or more artifacts in one or more images may include: a light source that operates to produce a light; an interference optical system that operates to: (i) receive and divide the light from the light source into a first light with which an object or sample is to be irradiated and a second reference light, (ii) send the second reference light for reflection off of a reference mirror of the interference optical system, and (iii) generate interference light by causing reflected or scattered light of the first light with which the object or sample has been irradiated and the reflected second reference light to combine or recombine, and/or to interfere, with each other, the interference light generating one or more interference patterns; and one or more detectors that operate to continuously acquire the interference light and/or the one or more interference patterns such that the one or more lumen edges and/or the one or more artifacts are detected in the images, and the one or more artifacts are removed from the one or more images.

In one or more embodiments, a method for detecting one or more lumen edges and one or more artifacts in at least one image may include: filtering two dimensional (2D) image data to smooth at least one image of a target or object; computing vertical and horizontal gradients of the at least one image; performing one dimensional (1D) filtering to smooth A-line data and gradients in each direction along each A-line; determining or detecting a significant pulse for each A-line, and detecting a lumen edge point in each A-line from the significant pulse; and forming one or more complete lumen edges from the at least one image.

In one or more embodiments, a computer-readable storage medium storing at least one program that operates to cause one or more processors to execute a method for detecting one or more lumen edges and one or more artifacts in at least one image, where the method may include: filtering two dimensional (2D) image data to smooth at least one image of a target or object; computing vertical and horizontal gradients of the at least one image; performing one dimensional (1D) filtering to smooth A-line data and gradients in each direction; determining or detecting a significant pulse for each A-line as a lumen edge, or detecting a lumen edge point in each A-line from the significant pulse; and forming one or more complete lumen edges from the at least one image.

In accordance with one or more embodiments of the present disclosure, apparatuses and systems, and methods and storage mediums for lumen and artifacts detection in one or more images may operate to characterize biological objects, such as, but not limited to, blood, mucus, tissue, etc.

It should be noted that one or more embodiments of the lumen and artifact detection method(s) of the present disclosure may be used in other imaging systems, apparatuses or devices, where images are formed from signal reflection and scattering within tissue sample(s) using a scanning probe. For example, IVUS images may be processed in addition to or instead of OCT images.

One or more embodiments of the present disclosure may be used in clinical application(s), such as, but not limited to, intervascular imaging, atherosclerotic plaque assessment, cardiac stent evaluation, balloon sinuplasty, sinus stenting, arthroscopy, ophthalmology, ear research, veterinary use and research, etc.

In accordance with at least another aspect of the present disclosure, one or more technique(s) discussed herein may be employed to reduce the cost of at least one of manufacture and maintenance of the one or more apparatuses, devices, systems and storage mediums by reducing or minimizing a number of optical components and by virtue of the efficient techniques to cut down cost of use/manufacture of such apparatuses, devices, systems and storage mediums.

According to other aspects of the present disclosure, one or more additional devices, one or more systems, one or more methods and one or more storage mediums using, or for use with, one or more lumen edges and artifacts detection techniques are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIGS. 7A-7B are graphs showing an A-line from a guidewire (solid line) and its gradient (dashed line) and showing an A-line from a stent (solid line) and its gradient (dashed line), respectively, in accordance with one or more aspects of the present disclosure;

FIG. 17 shows a schematic diagram of an embodiment of a computer that may be used with one or more embodiments of at least one apparatus, system, method and/or storage medium, for performing lumen and artifacts detection techniques in accordance with one or more aspects of the present disclosure; and FIG. 18 shows a schematic diagram of another embodiment of a computer that may be used with one or more embodiments of at least one apparatus, system, method and/or storage medium, for performing lumen and artifacts detection techniques in accordance with one or more aspects of the present disclosure.

DETAILED DESCRIPTION OF THE PRESENT INVENTION

One or more devices/apparatuses, optical systems, methods and storage mediums for imaging using lumen and artifacts detection techniques are disclosed herein.

Figure 1:
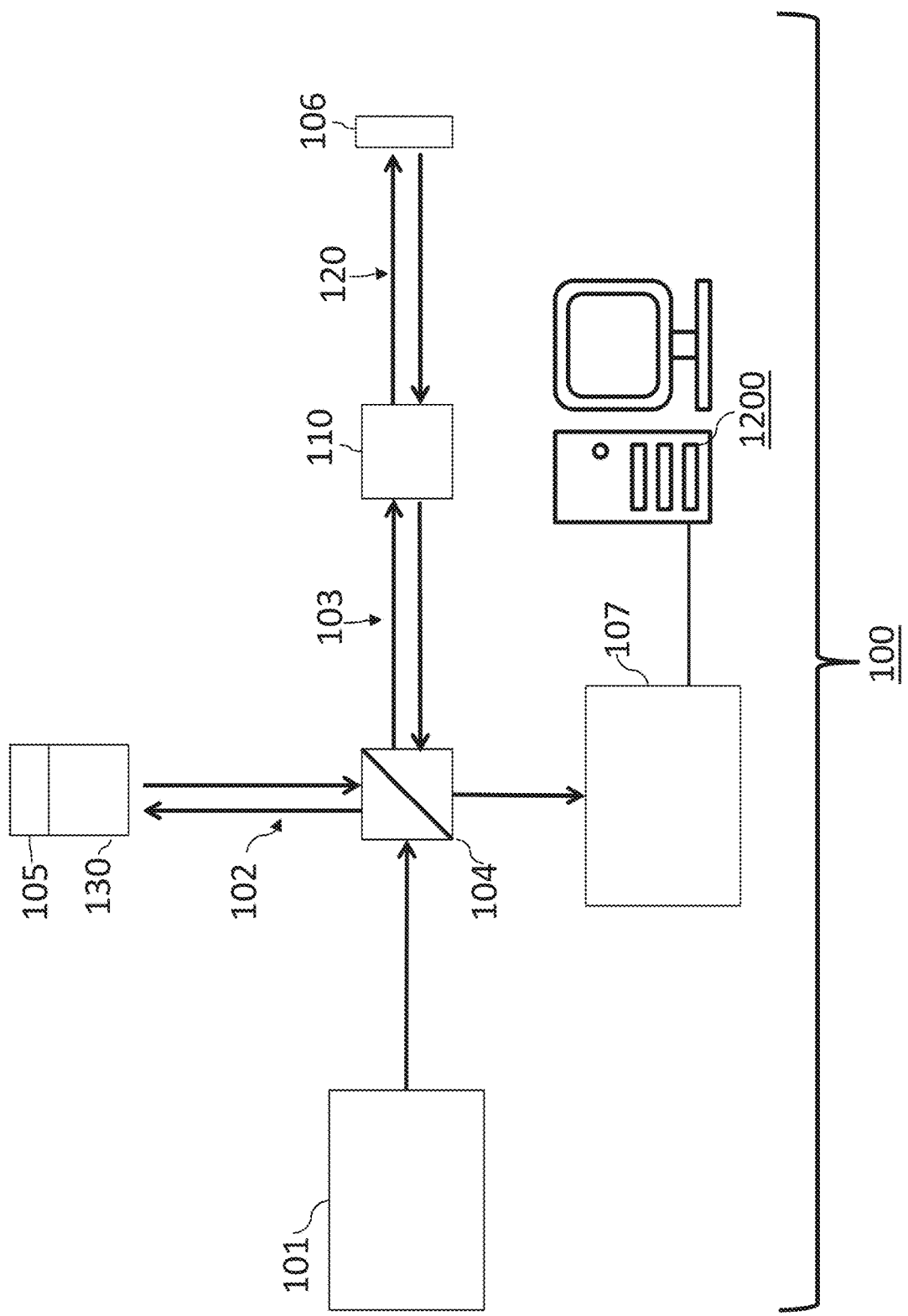
FIG. 1 is a diagram showing an embodiment of a system which can utilize one or more lumen edges and artifacts detection techniques in accordance with one or more aspects of the present disclosure.

Turning now to the details of the figures, FIG. 1 shows an OCT system 100 (as referred to herein as "system 100" or "the system 100") which operates to utilize an OCT technique, including, but not limited to, one or more embodiments of lumen and artifacts detection techniques discussed herein, with optical probe applications in accordance with one or more aspects of the present disclosure. The system 100 comprises a light source 101, a reference arm 102, a sample arm 103, a splitter 104 (also referred to herein as a "beam splitter"), a reference mirror (also referred to herein as a "reference reflection") 105, and one or more detectors 107. The system 100 may include a phase shift device or unit 130, and, in one or more embodiments, the phase shift device or unit may be omitted. In one or more embodiments, the system 100 may include a patient interface device or unit ("PIU") 110 and a catheter 120 (as diagrammatically shown in FIGS. 1-2), and the system 100 may interact with a sample or target 106 (e.g., via the catheter 120 and/or the PIU 110). In one or more embodiments, the system 100 includes an interferometer, or an interferometer is defined by one or more components of the system 100, such as, but not limited to, at least the light source 101, the reference arm 102, the sample arm 103, the splitter 104 and the reference mirror 105.

The light source 101 operates to produce a light to the splitter 104, which splits the light from the light source 101 into a reference beam passing into the reference arm 102 and a sample beam passing into the sample arm 103. The beam splitter 104 is positioned or disposed at an angle to the reference mirror 105, the one or more detectors 107 and to the sample or target 106. The reference beam goes through the phase shift unit 130 (when included in a system, as shown in the system 100), and the reference beam is reflected from the reference mirror 105 in the reference arm 102 while the sample beam is reflected or scattered from a sample 106 through the PIU (patient interface unit) 110 and the catheter 120 in the sample arm 103. Both of the reference and sample beams combine (or recombine) at the splitter 104 and generate interference patterns. The output of the system 100 and/or the interferometer thereof is continuously acquired with the one or more detectors 107, e.g., such as, but not limited to, photodiodes or multi-array cameras. The one or more detectors 107 measure the interference or interference patterns between the two radiation or light beams that are combined or recombined. In one or more embodiments, the reference and sample beams have traveled different optical path lengths such that a fringe effect is created and is measurable by the one or more detectors 107. Electrical analog signals obtained from the output of the system 100 and/or the interferometer thereof are converted to digital signals to be analyzed with a computer, such as, but not limited to, the computer 1200, 1200' (shown in FIG. 17 or FIG. 18, respectively, discussed further below). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

The light source 101 may include a plurality of light sources or may be a single light source. The light source 101 generates broadband laser lights in one or more embodiments. The light source 101 may include one or more of a laser, an organic Light-Emitting Diode (OLED), a Light-Emitting Diode (LED), a halogen lamp, an incandescent lamp, supercontinuum light source pumped by a laser, and/or a fluorescent lamp. The light source 101 may be any light source that provides light which can then be split up into at least three bands in which each band is further dispersed to provide light which is then used to for spectral encoding of spatial information. The light source 101 may be fiber coupled or may be free space coupled to the other components of the system or systems discussed herein, such as, but not limited to, the system 100, the system 100', the system 100'', the system 100''', etc.

In accordance with at least one aspect of the present disclosure, a feature of OCT systems is implemented using fiber optics. As aforementioned, one application of an OCT technique of the present disclosure is to use OCT with a catheter 120 as schematically shown in FIGS. 1-2.

Figure 2:
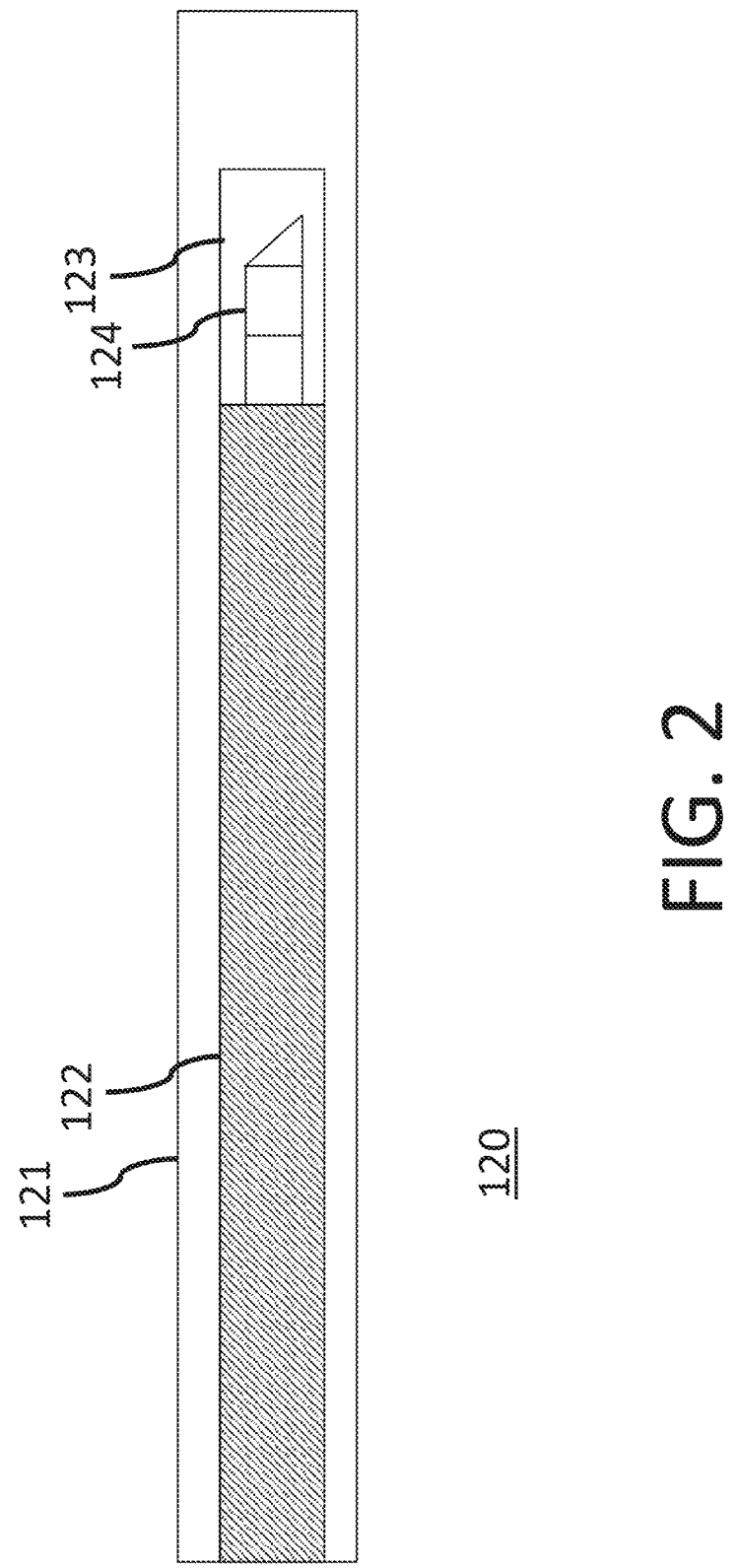
FIG. 2 is a diagram of an embodiment of a catheter that may be used with at least one embodiment of an apparatus or system for performing lumen and artifacts detection techniques in accordance with one or more aspects of the present disclosure.

FIG. 2 shows an embodiment of the catheter 120 including a sheath 121, a coil 122, a protector 123 and an optical probe 124. As shown schematically in FIGS. 1-2, the catheter 120 preferably is connected to the PIU 110 to spin the coil 122 with pullback (e.g., at least one embodiment of the PIU 110 operates to spin the coil 122 with pullback). The coil 122 delivers torque from a proximal end to a distal end thereof (e.g., via or by a rotational motor in the PIU 110). In one or more embodiments, the coil 122 is fixed with/to the optical probe 124 so that a distal tip of the optical probe 124 also spins to see an omnidirectional view of a biological organ, sample or material being evaluated, such as, but not limited to, hollow organs such as vessels, a heart, etc. For example, fiber optic catheters and endoscopes may reside in the sample arm (such as the sample arm 103 as shown in FIG. 1) of an OCT interferometer in order to provide access to internal organs, such as intravascular images, gastrointestinal tract or any other narrow area, that are difficult to access. As the beam of light through the optical probe 124 inside of the catheter 120 or endoscope is rotated across the surface of interest, cross-sectional images of one or more samples are obtained. In order to acquire three-dimensional data, the optical probe 124 is simultaneously translated longitudinally during the rotational spin resulting in a helical scanning pattern. This translation may be performed by pulling the tip of the probe 124 back towards the proximal end and therefore referred to as a pullback.

In one or more embodiments, the patient user interface 110 may comprise or include a connection component (or interface module), such as a rotary junction, to connect one or more components, such as one or more components of a probe (e.g., a catheter 120 (see e.g., FIGS. 1-2)), a needle, a capsule, a patient interface unit (e.g., the patient interface unit 110), etc., to one or more other components, such as, an optical component, a light source (e.g., the light source 101), a deflection section (e.g., such as the deflection or deflected section, which is a component that operates to deflect the light from the light source to the interference optical system, and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; etc.), the sample arm 102, a motor that operates to power the connection component and/or the patient user interface 110, etc. For example, when the connection member or interface module is a rotary junction, preferably the rotary junction operates as discussed below). In one or more other embodiments, the rotary junction may be at least one of: a contact rotary junction, a lenseless rotary junction, a lens-based rotary junction, or other rotary junction known to those skilled in the art.

In at least one embodiment, the PIU 110 may include a Fiber Optic Rotary Junction (FORJ), a rotational motor and translation motorized stage (e.g., a portion of the PIU 110), and a catheter connector (e.g., a portion of the PIU 110). The FORJ allows uninterrupted transmission of an optical signal while rotating a fiber along the fiber axis. The FORJ may have a free space optical beam combiner including a rotor and stator.

Descriptions of like-numbered elements present in the system 1000' and already described above, such as for the system 100, shall not be repeated, and are incorporated by reference herein in their entireties.

In at least one embodiment, the console 1200, 1200' operates to control motions of a motor and translation motorized stage (hereinafter referred to as "motor" or "motor and stage"), acquires intensity data from the at least one detector(s) 107, and displays the scanned image (e.g., on a monitor or screen such as a display, screen or monitor 1209 as shown in the console 1200 of FIG. 17 and/or the console 1200' of FIG. 18 as further discussed below). In one or more embodiments, the console 1200, 1200' operates to change a speed of the motor and/or to stop the motor. The motor may be a stepping or a DC servo motor to control the speed and increase position accuracy.

In one or more embodiments, the console or computer 1200, 1200' operates to control the system 100 (and other systems, such as, but not limited to, the system 100', the system 100", the system 100''', etc. as discussed further below), the catheter 120 and/or one or more other above-described components of the system 100. In at least one embodiment, the console or computer 1200, 1200' operates to acquire intensity data from the at least one detector 107 of the OCT system/device/apparatus, and displays the image(s) (e.g., on a monitor or screen such as a display, screen or monitor 1209 as shown in the console 1200 of FIG. 17 and/or the console 1200' of FIG. 18 as further discussed below). The output of the one or more components of the system 100 (and other systems, such as, but not limited to, the system 100', the system 100", the system 100''', etc. as discussed further below) is acquired with the at least one detector 107 of the OCT system/device/apparatus, e.g., such as, but not limited to, photodiodes, Photomultiplier tube(s) (PMTs), line scan camera(s), or multi-array camera(s). Electrical analog signals obtained from the output of the system 100 (and/or other systems, such as, but not limited to, the system 100', the system 100", the system 100''', etc. as discussed further below) or one or more components thereof are converted to digital signals to be analyzed with a computer, such as, but not limited to, the computer 1200, 1200' (e.g., as shown in FIGS. 1, 14, 16 and 17-18). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum. In some embodiments, the at least one detector 107 comprises three detectors configured to detect three different bands of light.

Figure 3A:
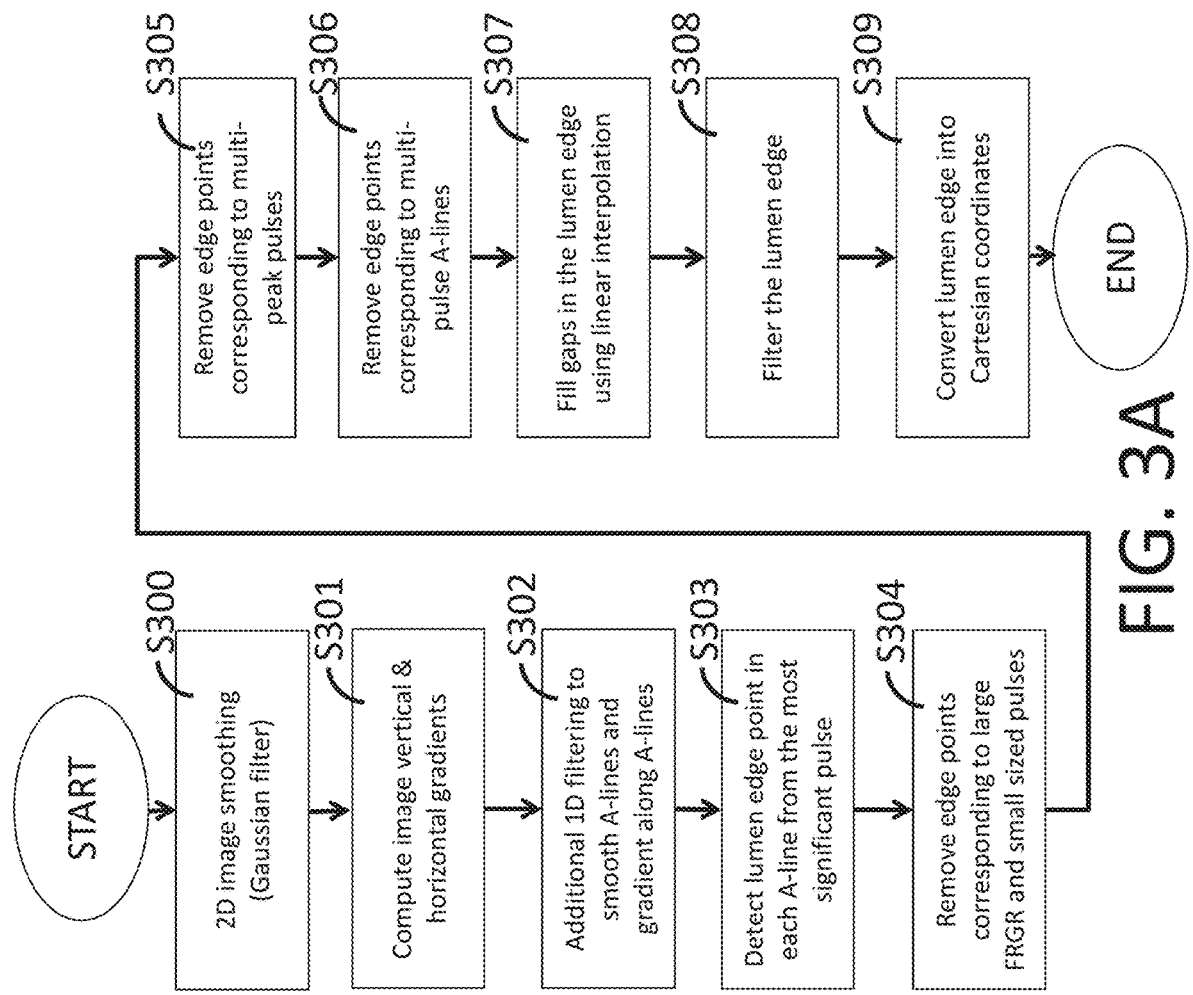
FIGS. 3A-3B are flow diagrams showing respective embodiments of at least two lumen and artifacts detection processes in accordance with one or more aspects of the present disclosure.

In accordance with at least one aspect of the present disclosure and as aforementioned, one or more methods for lumen and artifacts detection of OCT images are provided herein. FIG. 3A illustrates a flow chart of at least one embodiment of a method for lumen and artifacts detection of OCT image(s). Preferably, the method(s) may include one or more of the following: (i) performing two dimensional (2D) image smoothing (e.g., using a lowpass filter, using a Gaussian filter, etc.) (see step 300 of FIG. 3A); (ii) computing image vertical and horizontal gradients (see step S301 of FIG. 3A); (iii) smoothing A-lines and gradient along A-lines (e.g., using one dimensional (1D) filtering) (see step S302 of FIG. 3A); (iv) detecting a lumen edge point(s) in each A-line from the most significant pulse (e.g., the most significant pulse may be the pulse with the highest amplitude or the pulse with the largest underlying area determined by applying a size criterion or size criteria (e.g., width criterion, area under the pulse criterion, etc.) where different size criteria may produce similar results) (see step S303 of FIG. 3A); (v) removing edge points corresponding to a large falling and rising gradient ratio (FRGR) (e.g., the most significant pulse in the A-line that has a steep falling edge comparable to the rising edge, that produces a larger FRGR value, etc.) and small sized pulses (e.g., the most significant pulse in the A-line with the pulse amplitude or the area underlying the pulse below a threshold, etc.) (see step S304 of FIG. 3A); (vi) removing edge point(s) corresponding to multi-peak pulse(s) (see step S305 of FIG. 3A); (vii) removing edge point(s) corresponding to multi-pulse A-line(s) (see step S306 of FIG. 3A); (viii) filling the gaps in the lumen edge using interpolation (e.g., via median filtering the lumen edge) to form the lumen edge (e.g., forming the lumen edge from the most significant pulse locations of all the A-lines) (see step S307 of FIG. 3A); (ix) filtering or smoothing the lumen edge (e.g., using low pass filtering, such as 1D lowpass filtering and/or median filtering, etc.) (see step S308 of FIG. 3A); and (x) converting the lumen edge into Cartesian coordinates (see step S309 of FIG. 3A).

In one or more OCT images of a stented vessel in the polar coordinates (best shown in different lumen detection embodiment examples, including, the images of FIGS. 4A, 4C, 4E, 4G and 4I), the center of the imaging probe may be located at the top edge of the image. Each column of the image constitutes an A-line in one or more embodiments. Preferably, in at least one embodiment, the OCT image in polar coordinates is filtered using a two dimensional low pass Gaussian filter (see e.g., step S300 in FIG. 3A) to smooth out the inter A-line noise as well as some of the intra A-line noise in order to reduce and/or remove the overall noise in the image.

In one or more method embodiments, image vertical and horizontal gradients are preferably computed (see step S300 of FIG. 3A). In one or more embodiments, a convolution operation operator Kernel (K), may be used such that G=K⊗A, where ⊗ denotes a convolution operation. In at least one embodiment, the vertical gradient of the image may be calculated, for example, by applying the vertical Sobel operator (e.g., as one embodiment example of the Kernel K) to the smoothed image obtained from step S300:

$$G_y = \begin{bmatrix} 1 & 4 & 6 & 4 & 1 \\ 2 & 8 & 12 & 8 & 2 \\ 0 & 0 & 0 & 0 & 0 \\ -2 & -8 & -12 & -8 & -2 \\ -1 & -4 & -6 & -4 & -1 \end{bmatrix} \otimes A,$$

where A is the smoothed image from [Step 1], $G_x$ and $G_y$ are the horizontal and vertical gradients, and ⊗ denotes the 2D convolution operation. In at least one embodiment, the horizontal gradient of the image may be calculated, for example, by applying the horizontal Sobel operator (e.g., as one embodiment example of the Kernel K) to the smoothed image obtained from step S300:

$$G_x = \begin{bmatrix} -1 & -2 & 0 & 2 & 1 \\ -4 & -8 & 0 & 8 & 4 \\ -6 & -12 & 0 & 12 & 6 \\ -4 & -8 & 0 & 8 & 4 \\ -1 & -2 & 0 & 2 & 1 \end{bmatrix} \otimes A,$$

where A is the smoothed image from [Step 1], $G_x$ and $G_y$ are the horizontal and vertical gradients, and ⊗ denotes the 2D convolution operation. Each column in $G_y$ provides the gradient along an A-line while each row in $G_x$ provides the gradient across A-lines. The image vertical and horizontal gradients may also be computed using lower order Sobel operators as:

$$G_x = \begin{bmatrix} -1 & 0 & 1 \\ -2 & 0 & 2 \\ -1 & 0 & 1 \end{bmatrix} \otimes A, \text{ and}$$

$$G_y = \begin{bmatrix} 1 & 2 & 1 \\ 0 & 0 & 0 \\ -1 & -2 & -1 \end{bmatrix} \otimes A,$$

wherein A is the smoothed at least one image, $G_x$ and $G_y$ are the horizontal and vertical gradients, ⊗ denotes a two dimensional (2D) convolution operation, and each column in $G_y$ provides the gradient along an A-line while each row in $G_x$ provides the gradient across A-lines. Other possible operators that may be used here are the Prewitt operators as:

$$G_x = \begin{bmatrix} -1 & 0 & 1 \\ -1 & 0 & 1 \\ -1 & 0 & 1 \end{bmatrix} \otimes A, \text{ and}$$

$$G_y = \begin{bmatrix} 1 & 1 & 1 \\ 0 & 0 & 0 \\ -1 & -1 & -1 \end{bmatrix} \otimes A,$$

wherein A is the smoothed at least one image, $G_x$ and $G_y$ are the horizontal and vertical gradients, ⊗ denotes a two dimensional (2D) convolution operation, and each column in $G_y$ provides the gradient along an A-line while each row in $G_x$ provides the gradient across A-lines.

Figure 5:
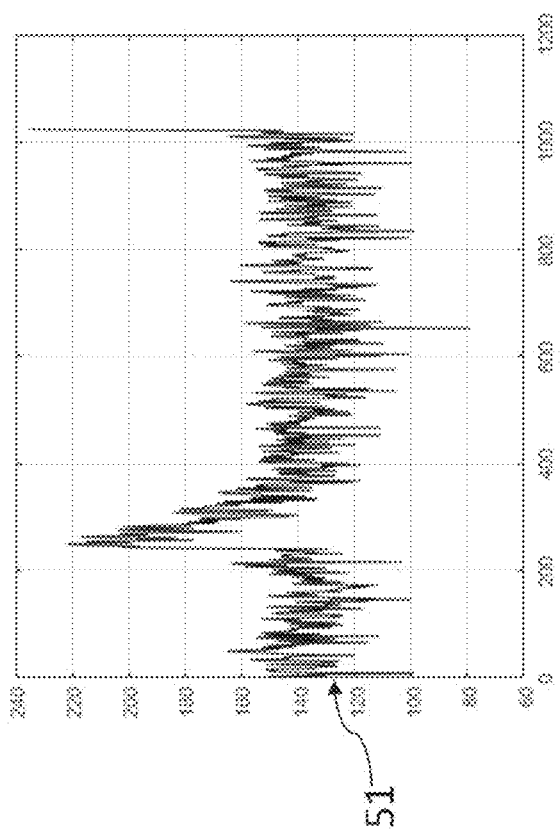
FIG. 5 is a graph showing a raw A-line signal from a target (e.g., soft tissue) without filtering in accordance with one or more aspects of the present disclosure.

In one or more method embodiments, additional filtering (e.g., 1D filtering) may be performed to smooth A-lines and gradient(s) along A-lines (see step S302) of FIG. 3A. In at least one embodiment, it should be noted that soft tissue has a wide bright region beyond the lumen edge while artifacts produce an abrupt dark shadow area beyond the edge. A typical A-line from the soft tissue may be plotted as a one dimensional signal 51 as shown in FIG. 5. The pulse in the one dimensional signal corresponds to the vessel wall. The rising edge of the pulse is where the edge pixel of the A-line lies. By detecting the edge pixel in each A-line, the two dimensional edge detection issue is converted into a simpler one dimensional pulse detection issue. In other words, one or more embodiments of the present disclosure simplify the lumen edge and artifacts detection approach and provide a solution at the same time.

Taking advantage of the flexibility in 1D signal processing, low pass and high pass 1D filtering may be applied to the A-line signal, in one or more embodiments, to remove the signal offset as well as to further smooth the A-line signal for more reliable pulse detection. The corresponding gradient along the A-line also may be filtered using a 1D filter for further smoothing. Preferably, any phase delay introduced by any filtering is avoided so that the pulse location is not shifted. For example, each A-line may be independently processed by applying 1D high pass filtering to remove a background and by applying low pass filtering to reduce noise.

Figure 6:
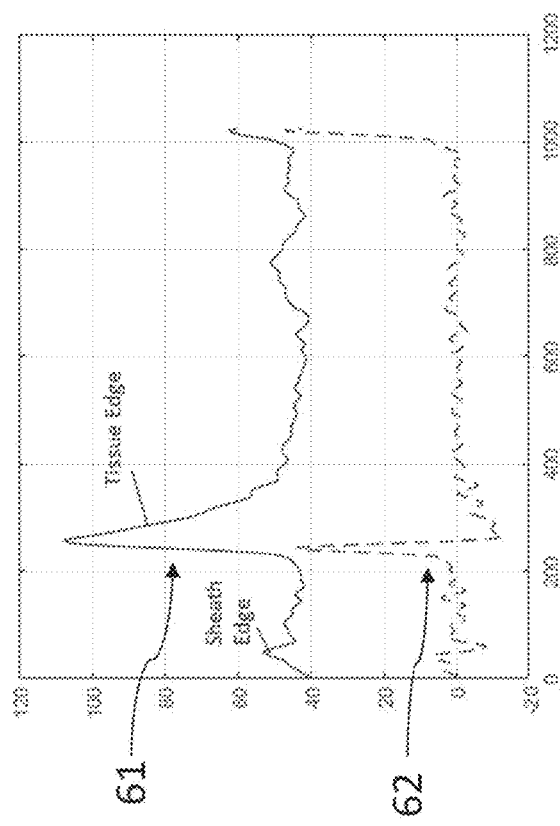
FIG. 6 is a graph showing smoothed A-line and gradient from a target (e.g., soft tissue) in accordance with one or more aspects of the present disclosure.

After such filtering, a much smoother A-line signal may be obtained as shown by the solid line 61 in FIG. 6. The smoothed one dimensional gradient along the A-line is also plotted (see dashed line 62) in FIG. 6 to show the correspondence between pixel intensity and the one dimensional gradient along the A-line. In one or more embodiments (see e.g., FIG. 6), the Y axis may be shown with arbitrary units (A.U.), and a pixel index (e.g., about 7 micron per pixel, about 5 micron per pixel, etc.) may be used for the X axis. As shown in FIG. 6, the lumen edge pixel is located at the rising edge of the intensity signal, which corresponds to the maximum peak location in the one dimensional gradient signal. Signals from the catheter sheath also may be noticed in the smoothed A-line signal (see Sheath Edge designation in FIG. 6), and the catheter sheath signal has much lower amplitude compared to that of the lumen edge signal.

In one or more method embodiments, detection of the lumen edge point in each A-line from the most significant pulse may be performed to create lumen edge data (see step S303) of FIG. 3A. In one or more embodiments, the lumen edge data may contain or include artifact edge pixels. There are numerous ways to perform this step. For example, for each A-line signal, the most significant pulse therein may be detected using an adaptive threshold. Based on the mean and the maximum values of the smoothed A-line, a simple threshold may be computed as:

$$Threshold=(mean+peak)/2,$$

where "mean" is the average of the smoothed A-line and "peak" is the maximum value of the smoothed A-line.

As a further example, another approach to find the threshold is to find the average between the max peak and min peak as:

$$Threshold=(min+peak)/2.$$

A further alternative approach is to find the threshold based on the max peak as:

$$Threshold=(peak) \times 2/3.$$

Regardless of the approach, the predetermined or determined threshold is used to detect the most significant pulse corresponding to the lumen edge (in one or more embodiments, the lumen edge data may contain or include artifact edge pixels) in the specific A-line. Any pulse above the threshold is an edge pulse candidate. The largest pulse among all the candidates in terms of area under the pulse is considered to be the maximum peak (or the "most significant pulse"). The location of the highest peak of the one dimensional gradient signal along the A-line in the vicinity of the maximum peak is used to identify the exact location of the lumen edge point in the smoothed A-line. Again, in one or more embodiments, the lumen edge data may contain or include artifact edge pixels.

Placing together all the lumen edge points thus detected from all the A-lines forms the lumen edge (in one or more embodiments, the lumen edge data may contain or include artifact edge pixels) for the vessel as a function of maximum peak locations vs. A-line indices.

In one or more method embodiments, edge points corresponding to large FRGR and small sized pulses may be removed (see step S304) of FIG. 3A. In other words, artifact edge pixel(s) contained or included in the lumen edge pixel(s) may be removed using FRGR.

For example, in the presence of stent struts and guidewires, the lumen edge points of the soft tissue may be fully or partially obstructed. The lumen edge points detected from Step S303 may contain the edge points from the artifacts in the OCT image. In one or more embodiments, these edge points will distort the lumen geometric parameter calculation and preferably are removed before accurate or more accurate parameters may be obtained.

FIG. 7A depicts an example A-line from a guidewire (see smooth line 71; gradient of the A-line from the guidewire is shown by the dashed line 72). As seen in FIG. 7A, it is noticeable that the one-dimensional gradient signal (see dashed line 72) has a steep minimum peak, which corresponds to the sharp falling intensity of the A-line signal (see sold line 71) due to the opaqueness of the guidewire to the imaging laser beam and the relative large size of the guidewire. The width of the one dimensional pulse is much narrower as shown in FIG. 7A compared to the pulse signal from the soft tissue as shown in FIG. 6.

FIG. 7B depicts an example A-line from a stent strut (see smooth line 73; gradient of the A-line from the stent is shown by the dashed line 74). As seen in FIG. 7B, it should be noted that the pulse signal corresponding to the stent strut also produces a relatively larger falling peak compared to the rising peak in the one dimensional gradient signal, though it is less pronounced compared to that from the guidewire as shown in FIG. 7A.

Based on these signatures (as shown in FIGS. 7A-7B), the falling and rising gradient ratio (FRGR) is introduced as a measure of opaqueness and reflectivity of the imaged object or target. An A-line signal from a guidewire has a large falling and rising ratio, and so does an A-line from a stent strut. On the other hand, an A-line from the soft tissue has a smaller falling and rising gradient ratio. Table 1 lists the falling and rising gradient ratio values for the A-lines in FIGS. 6-7B.

TABLE 1

| Falling and Rising Gradient Ratio Values | | | |
|---|---|---|---|
| | A-line from Soft Tissue see line 61), FIG. 6 | A-line from Guidewire see line 71), FIG. 7A | A-line from Stent Strut (see line 73), FIG. 7B |
| Falling Rising Gradient Ratio | 0.20-0.45 | 0.80-0.97 | 0.50-0.80 |

Figure 8:
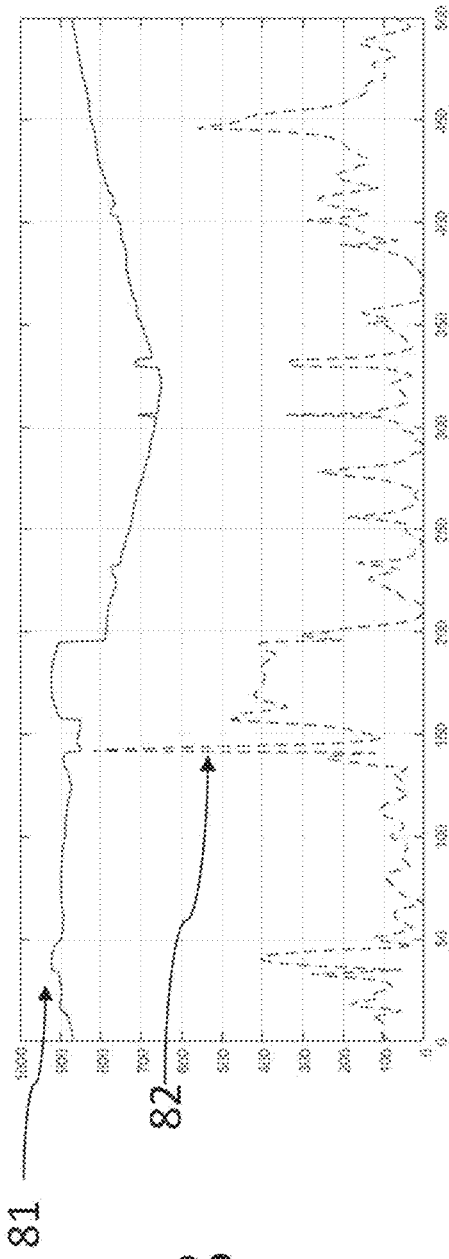
FIG. 8 is a graph showing a lumen edge (solid line) containing the artifact edge pixels and a falling rising gradient ratio (FRGR) (dashed line) in accordance with one or more aspects of the present disclosure.

The falling and rising gradient ratio may be used as an indicator of the stent strut and guidewire presence if the detected lumen edge (see solid line 81) and its corresponding falling rising gradient ratio (see dashed line 82) are plotted together as shown in FIG. 8. In one or more embodiments, the FRGR of the A-line from soft tissue may be 0.47 or 0.20 to 0.47. In one or more embodiments, the FRGR of the A-line from the stent strut may be 0.62.

Figure 9:
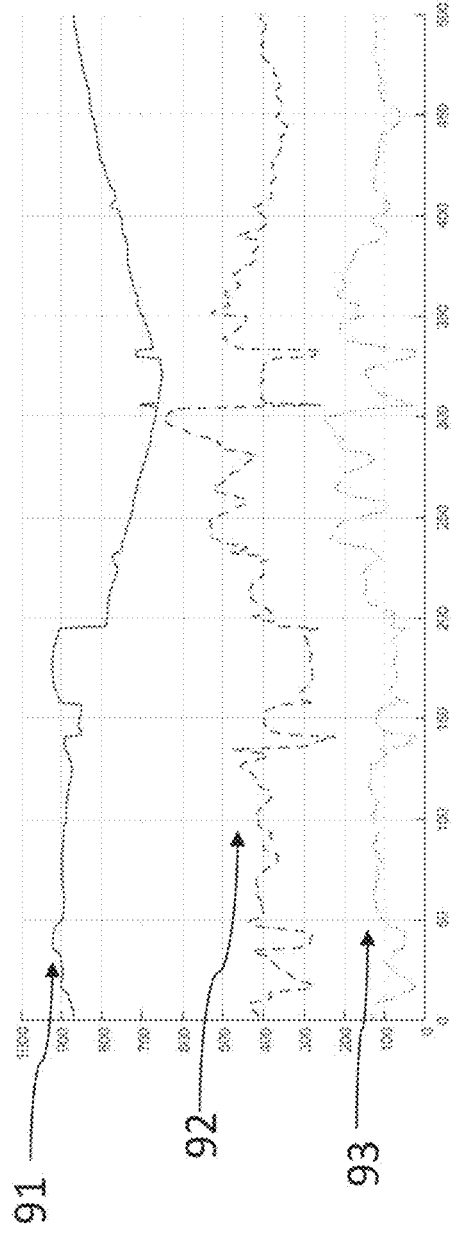
FIG. 9 is a graph showing a lumen edge (solid line) containing the artifact edge pixels, an A-line signal pulse width (dashed line) and a pulse area (dotted line) in accordance with one or more aspects of the present disclosure.

Besides the noticeable differences of falling and rising gradient ratio values in the A-line signals from artifacts and soft tissue, it should be noted that the pulse size from the soft tissue and the pulse size from the artifacts display a noticeable difference. In one or more embodiments, one may use either the pulse width (see e.g., A-signal pulse width dashed line 92 in FIG. 9) or the area under the 1D signal pulse (see e.g., pulse area dotted line 93 in FIG. 9) as the measure of the signal pulse size. The differences between the pulse size from the artifacts and the pulse size from the soft tissue become more apparent in the plot where the signal size and the detected lumen edge (see solid line 91 in FIG. 9) are plotted together as shown in FIG. 9.

Using the noticeable differences of the falling raising gradient ratio and the differences in a size of the A-line pulses, the artifact region locations corresponding to the guidewire and stent struts in the detected lumen edge may be identified using simple thresholding where the threshold may be set, for example, as:

$$\text{Pulse Size Threshold} = mean - sigma * k1$$

Or $$\text{FRGR Threshold} = mean + sigma * k2$$

where "mean" and "sigma" are the mean and standard deviation of the corresponding signal, and k1, k2 are empirical parameters preferably chosen, but not limited to, between 1 to 2.

An alternative approach to calculate the thresholds may be:

$$\text{Pulse Size Threshold} = mean + (peak - mean)/3$$

Or $$\text{FRGR Threshold} = mean + (peak - mean)/3$$

Furthermore, as another alternative, the thresholds may also be calculated as:

Pulse Size Threshold=peak−(peak−mean)/2

Or

FRGR Threshold=peak−(peak−mean)/2

Preferably, in one or more embodiments, these identified edge points are not considered as the lumen edge and are not used for lumen parameter calculation.

In one or more method embodiments, edge points corresponding to multi-peak pulses may be removed (see step S305) of FIG. 3A. At least two examples for performing this step are discussed herein. For example, lumen edge data that corresponds to the boundary region between the soft tissue and the stent struts or other artifacts may be removed using multi-peak pulses. However, such multi-peak pulses may present or be present in a non-boundary region as well. Then the average horizontal gradient(s) are/may be used to identify the non-boundary region in such cases.

There may be diffraction and scattering around the edges of stent struts and of the guidewire. The diffraction and scattering effect produces some boundary regions between the soft tissue and the artifacts where the detected lumen edge may be distorted. Furthermore, since the A-lines used for producing the lumen edge are preferably filtered using a 2D filter in step S300, the boundary regions may be further smeared and extended. To completely remove the artifact effects on the lumen edge, these boundary regions are preferably removed from the detected lumen edge.

Figure 10:
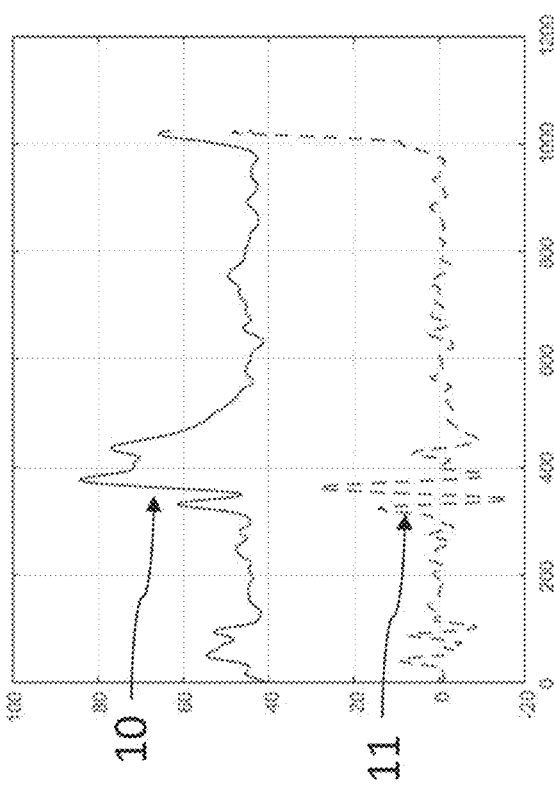
FIG. 10 is a graph showing an A-line from a boundary region between the soft tissue and a stent strut (solid line) and its gradient (dashed line) in accordance with one or more aspects of the present disclosure.

One advantage of using one dimensional A-line signal processing for lumen edge detection is that there may be a multi-peak pattern of these boundary regions from the A-line signal because both stents and lumen edge peaks exist in the A-line signal. For example, as shown in FIG. to, the boundary region produces clustered multi-peak pulses in the A-line signal (see solid line to in FIG. 10; see dashed line in FIG. to for the related gradient). Multi-peak pulses may be detected using the same threshold used in the maximum peak detection step S303 as discussed above, and is not repeated herein as a result. If a falling edge of a peak rises again before the falling edge falls below the threshold, a multi-peak pulse is considered to be identified in at least one embodiment. Preferably, if a pulse is detected as a multi-peak pulse, the lumen edge data from that A-line may be considered as the boundary region of the stent struts and guidewire and removed from lumen edge detection. In one or more embodiments, multi-peaks not in the boundary region may be retained, and are preferably retained in one or more embodiments.

Even if a falling edge of a peak falls below the threshold and then raises again to form another peak, it may still be considered as a multi-peak pulse. The correct identification of the lumen edge may then rely on the major peak detection and the size of the front peak in at least one embodiment. If the front peak is identified as the artifacts, such as, but not limited to, a stent or guidewire, the second peak may be the lumen edge. There may be small vessel branch presented in the tissue underneath the vessel wall, which may end up manifesting as two separate peaks in a single A-line in a similar manner in one or more embodiments. In such a case, the front peak without the narrow width may be the lumen edge. At least one way to distinguish multi-peak pulses between the valid lumen edge versus an influence of one or more artifacts is determining whether they are located within the boundary regions. Therefore, the multi-peak cases may be further classified into the non-boundary region and boundary region cases, and they may be removed from the detected lumen edge only in the boundary regions.

Figure 11:
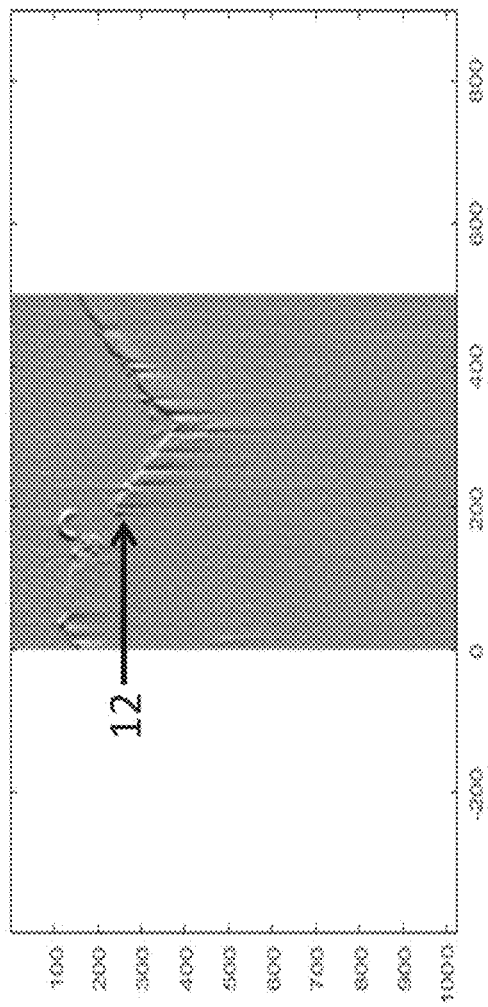
FIG. 11 is a plot of horizontal gradient image across A-lines in accordance with one or more aspects of the present disclosure.

By way of another example and alternative to the aforementioned example, horizontal gradients may be used to identify and remove the lumen edge data corresponding to the boundary region between the soft tissue and narrow artifacts. In at least one embodiment, another method to identify the boundary region utilizes the gradient variation along the horizontal direction in one or more of FIGS. 4A, 4C, 4E, 4G, 4I, etc. (figures in Polar Coordinate) (across the A-lines) in the region behind the detected lumen edge. As shown in FIG. 11, the gradient across the A-lines displays a pattern of many shadows caused by the light blocking artifacts. At least one example of an artifact shadow is shown by the arrow 12 in FIG. 11.

Figure 12:
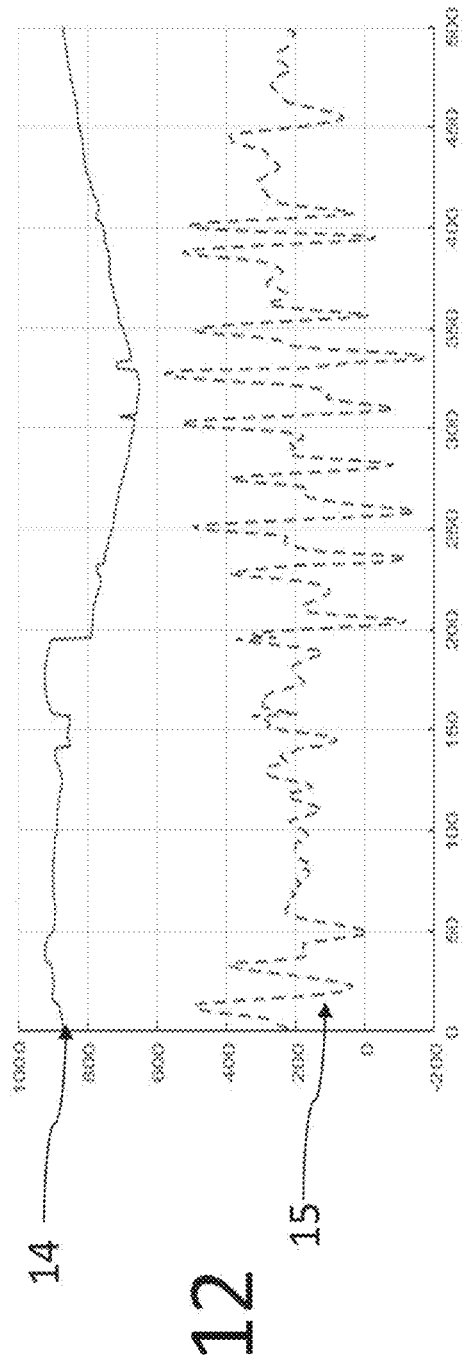
FIG. 12 is a graph showing a lumen edge (solid line) and a horizontal gradient variation (dashed line) around an edge in accordance with one or more aspects of the present disclosure.

For each detected lumen edge point, the average values of across the A-lines gradient below the edge point may be computed in FIG. 11. These average values reflect the locations of the shadows caused by the light blocking artifacts. Given the directional property of the gradient across the A-lines, the bright to dark edge produces a rising peak while the dark to bright edge produces a falling peak. For each dark shadow produced by the stent strut, the shadow is bordered by a rising peak at one side and by a falling edge at the other side. FIG. 12 shows the clear variation patterns of the across A-line gradient vs. the detected lumen edge (the lumen edge is shown via the solid line 14 and the across A-line gradient variation is shown via the dashed line 15 in FIG. 12).

The boundary regions may therefore be identified as the area surrounded by the rising and falling peaks in the averaged values of across A-lines gradient next to the immediate artifact regions identified in step S304. In step S304, thresholds may be used to identify the center locations of artifacts, and the boundary regions delineated by the falling and rising peaks in step S305 may help remove the artifact region more completely or completely. The boundary regions identified by the falling and rising peaks of the average horizontal gradient may be used to distinguish the multi-peak pulse that may or may not be associated with a boundary region, and, in one or more embodiments, only those multi-peak pulses falling inside the boundary region may be removed from the lumen edge detection.

In one or more method embodiments, edge points corresponding to multi-pulse A-lines may be removed (see step S306) of FIG. 3A. For example, lumen edge data corresponding to a ghost signal or ghost signals produced (e.g., from reflection(s) of stent(s), any signal(s) other than the targeted signal, a luminance signal, etc.) may be identified and removed by detecting multiple pulses.

Figure 13:
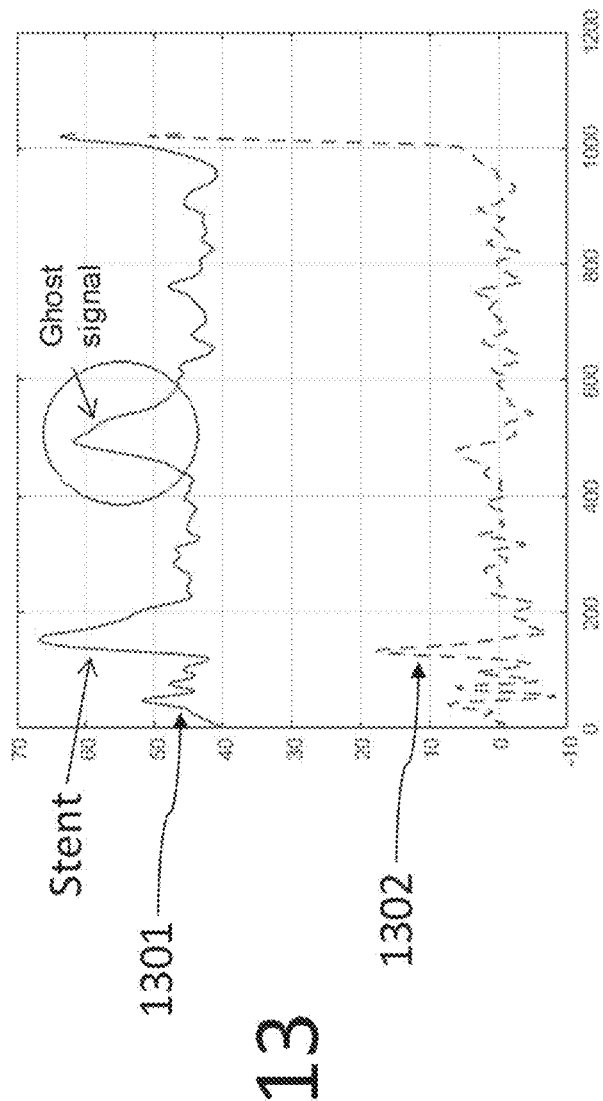
FIG. 13 is a graph showing an A-line with multipath reflection (solid line) and its gradient (dashed line) due to a stent strut in accordance with one or more aspects of the present disclosure.

When there is strong reflection caused by the stent struts or guidewire, there may be a ghost signal or signals in the A-line signal due to a detected multipath signal. As another advantage of using one dimensional A-line signal processing for lumen edge detection, this ghost signal (or signals) manifests itself as an additional pulse signal in the A-line signal. For example, an A-line plot in FIG. 13 (A-line signal with multipath reflection shown by the solid line 1301; the related gradient is shown via the dashed line 1302 in FIG. 13) shows two peaks in which the right peak corresponds to the ghost signal and the left peak corresponds to a stent strut. Peaks of all significant pulses in the A-line signal may be determined.

Given that the most likely sources of strong reflection are stent struts and guidewire, the detected lumen edge points corresponding to the A-lines with a ghost signal (or signals) are preferably excluded from the parameter calculation for the lumen.

In one or more method embodiments, a lumen edge may be formed (see step S307) of FIG. 3A. For example, after removing all the artifacts from the detected lumen edge (e.g., edge points with a narrow pulse width (which correspond to edge points from guide wire(s) and stent(s)) may be removed; edge points with large FRGR (which correspond to edge points from weak stent(s)) may be removed; edge points with separated multiple large pulses (which correspond to stents with a reflection image) may be removed; edge points with clustered multiple pulses (which correspond to the boundary of soft tissue and the stent(s)) may be removed; etc.), the gaps in the lumen edge may be filled using simple interpolation (e.g., linear interpolation) using the neighboring edge points. One embodiment example for doing this is to have the lumen edge undergo median filtering.

In one or more method embodiments, a lumen edge may be smoothed (see step S308) of FIG. 3A. For example, the lumen edge may undergo low pass filtering. In one or more embodiments, some simple median filtering and low pass filtering may be applied to lumen edge (edge locations vs. A-line pixels) to smooth and polish the final lumen edge.

In one or more method embodiments, a lumen edge may be converted into Cartesian coordinates (see step S309) of FIG. 3A.

At least one embodiment of a method for detecting lumen edges and artifacts may be summarized as follows: The OCT image in polar coordinates may be filtered using a two dimensional Gaussian filter to reduce the noise in the image. The separate gradient in vertical and horizontal directions may be computed using the Sobel filters from the filtered image. For each A-line, one dimensional filtering is applied to further smooth the A-line signal and remove the signal offset. The gradient along the A-line direction may be further smoothed using a low pass filter. For each A-line, all the significant pulses in the A-line signal may be found, and the most significant pulse and its position may be determined as the lumen data, based on the detection threshold and the pulse size using either pulse width or area under the pulse. The falling rising gradient ratio for the most significant pulse (lumen data) in each A-line may be computed. The lumen data may be removed, and a gap may be identified if the falling rising gradient ration is larger than the threshold value. The lumen data may be removed, and a gap may be identified if the pulse size is smaller than the threshold pulse size. The lumen data may be removed, and a gap may be identified if the detected pulses are multi-peak pulse(s) or where an artifact region detected from the previous step is bordered by the rising and falling peaks of the gradient across A-lines. The lumen data may be removed, and a gap may be identified if there is more than one comparable pulse in the A-line signal. Thereafter, the gaps are filled in the lumen edge using linear interpolation. Median filtering and/or low pass filtering may be applied to the lumen edge. The lumen edge may be converted into Cartesian coordinates for display.

Figure 3B:
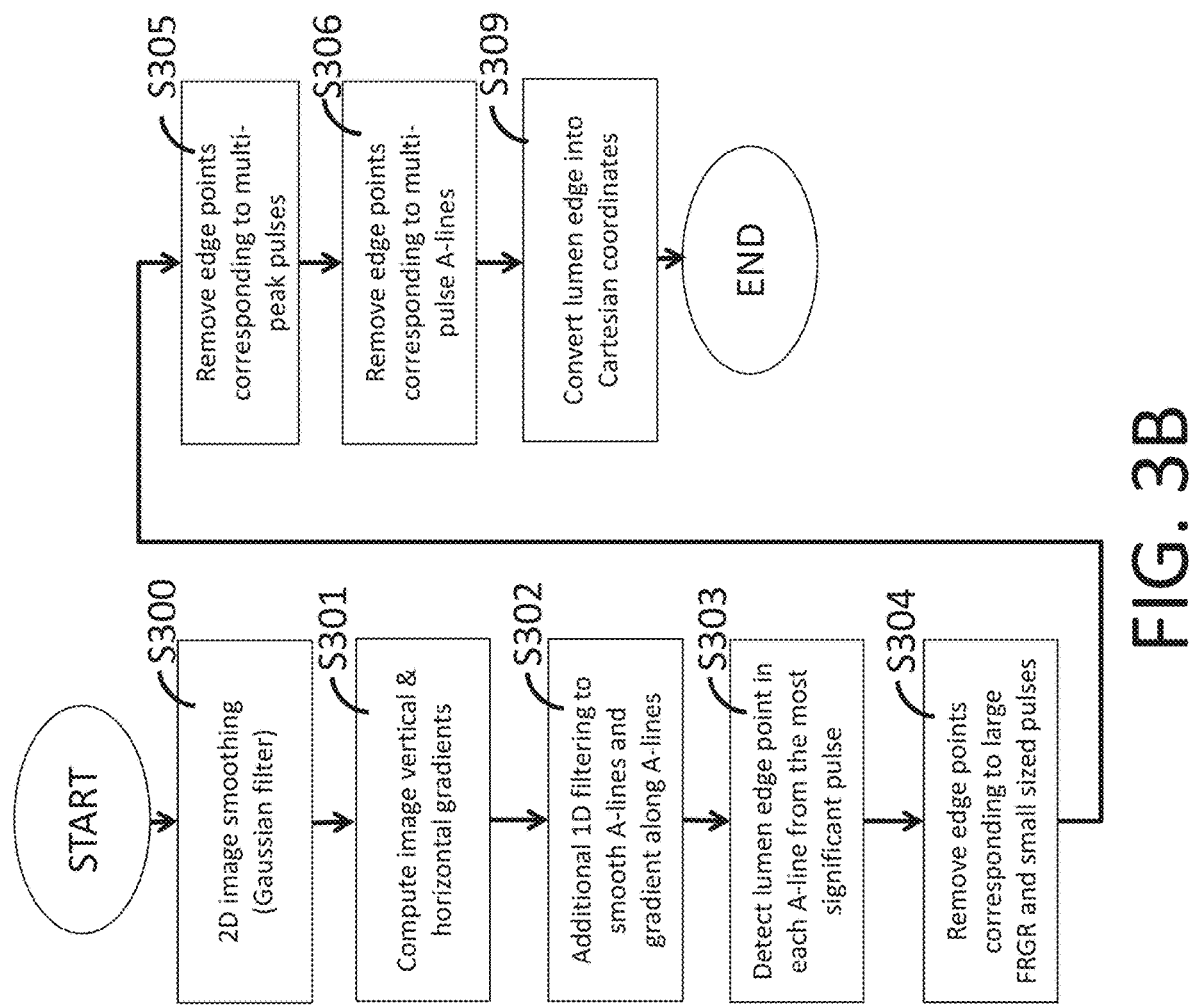
Figure 4B:
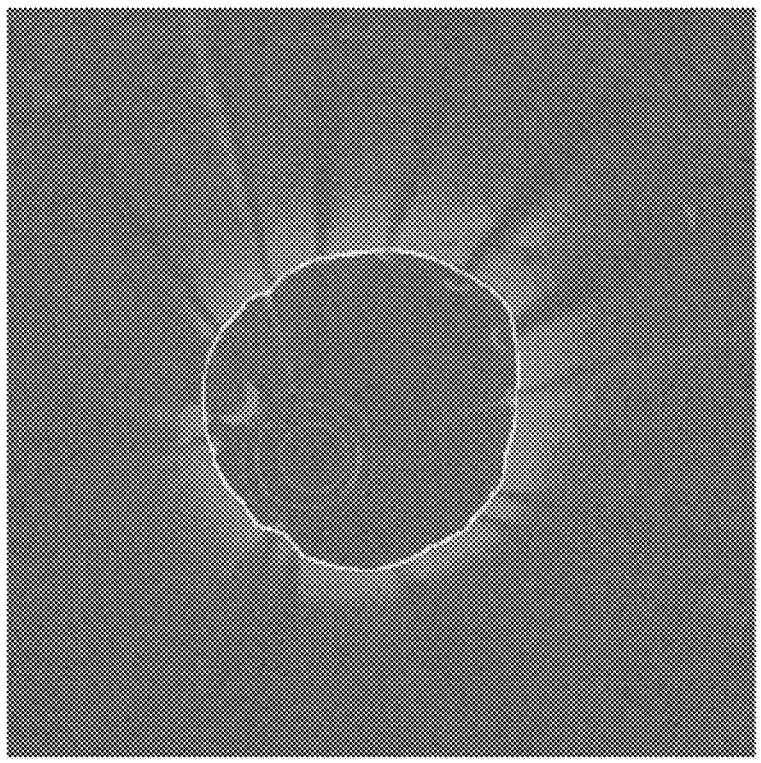
FIGS. 4A-4B, 4C-4D, 4E-4F, 4G-4H, and 4I-4J are respective pairs of an OCT image in Polar Coordinates taken of a target (e.g., a stented vessel) and an OCT image in Cartesian Coordinates, respectively, using at least one apparatus or system for performing lumen and artifacts detection techniques in accordance with one or more aspects of the present disclosure.
Figure 4A:
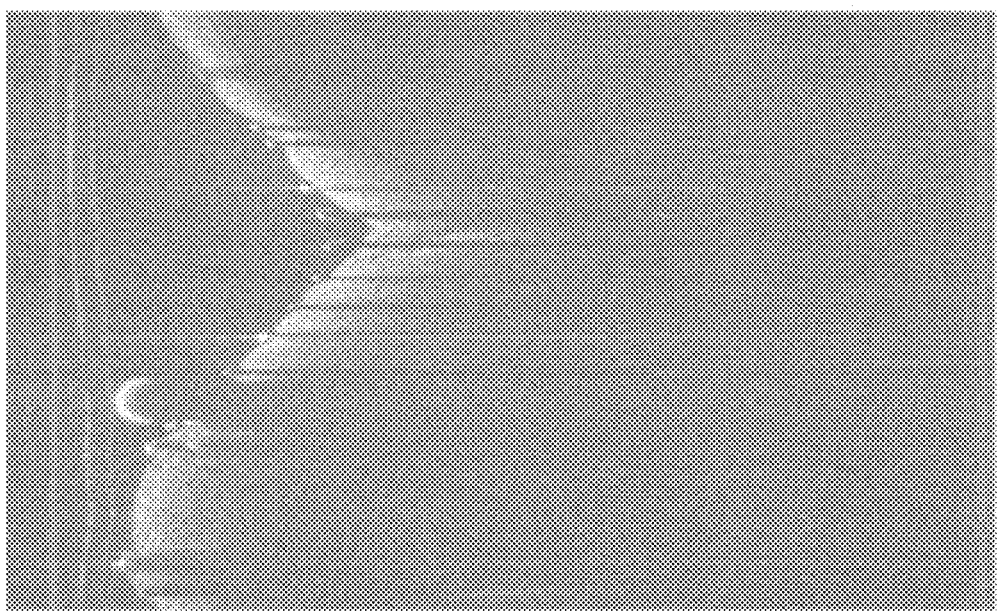
Figure 4D:
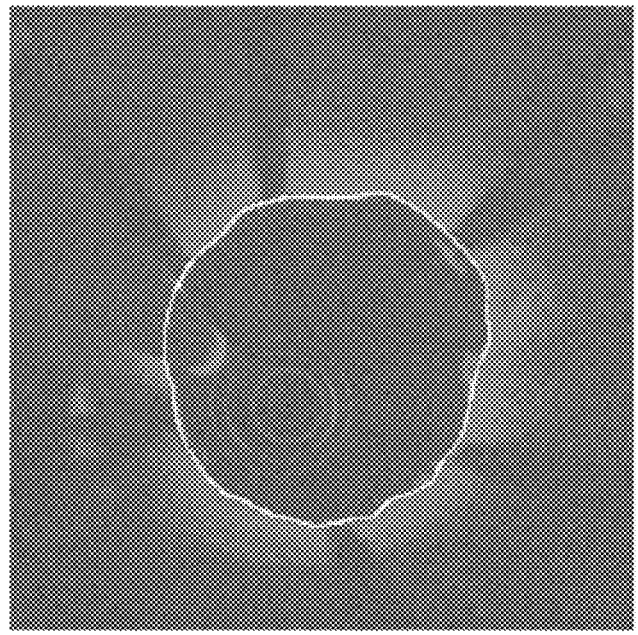
Figure 4C:
Figure 4F:
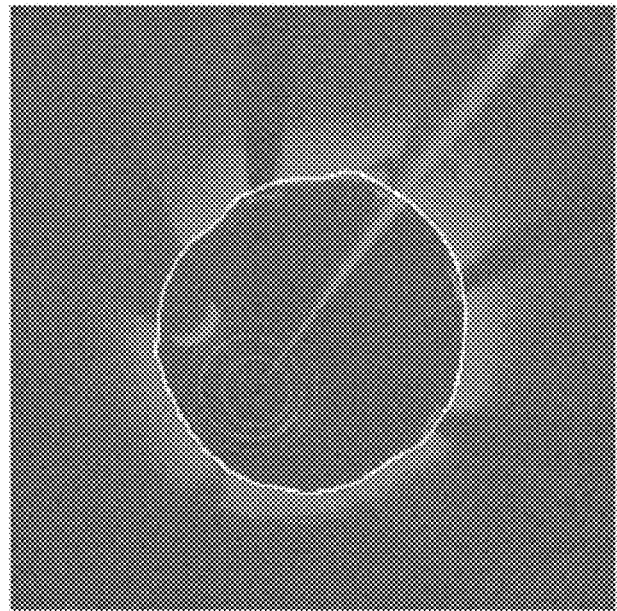
Figure 4E:
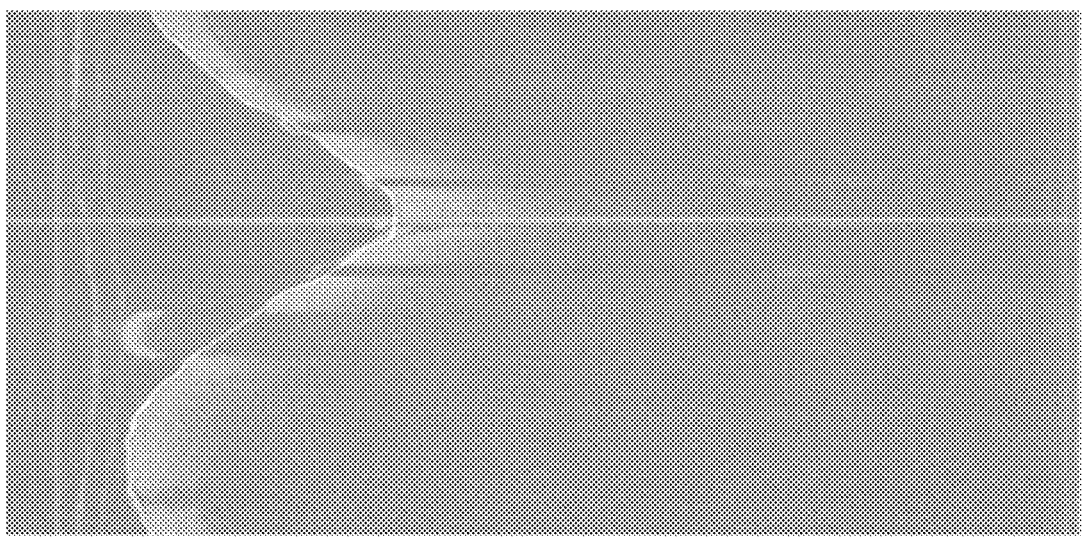
Figure 4H:
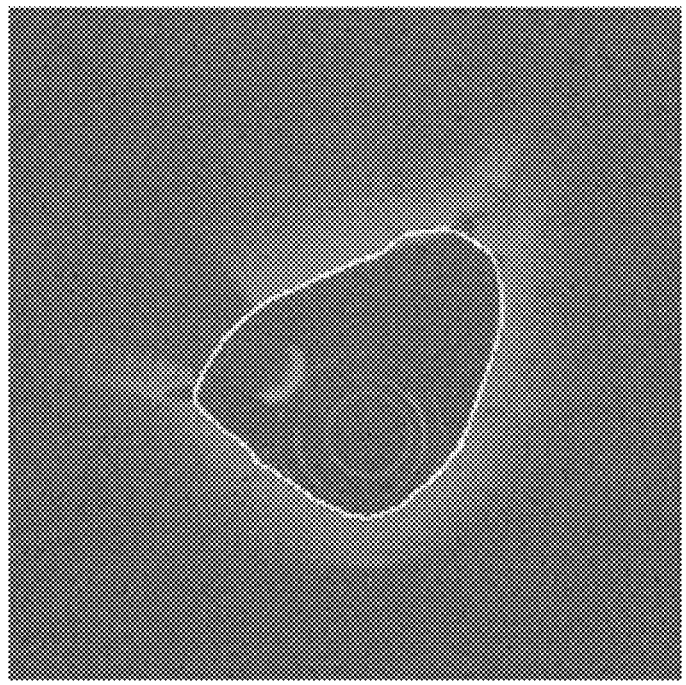
Figure 4G:
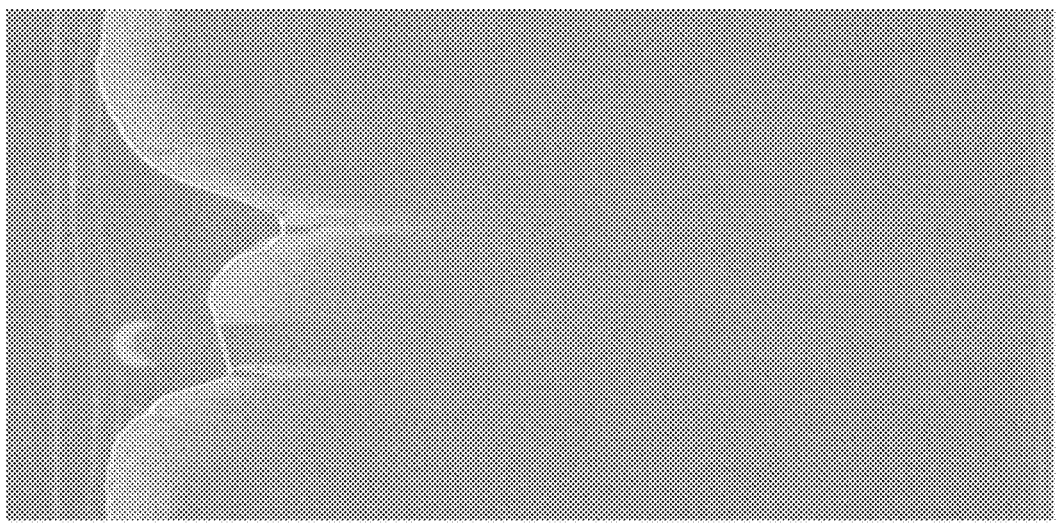
Figure 4J:
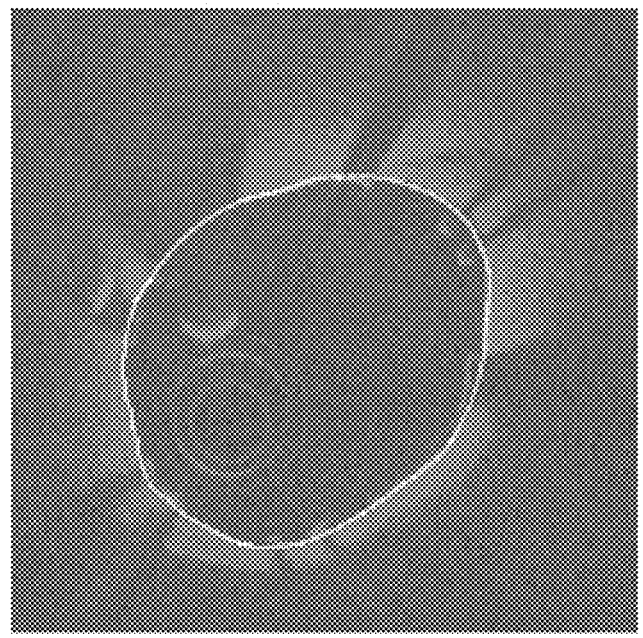
Figure 4I:
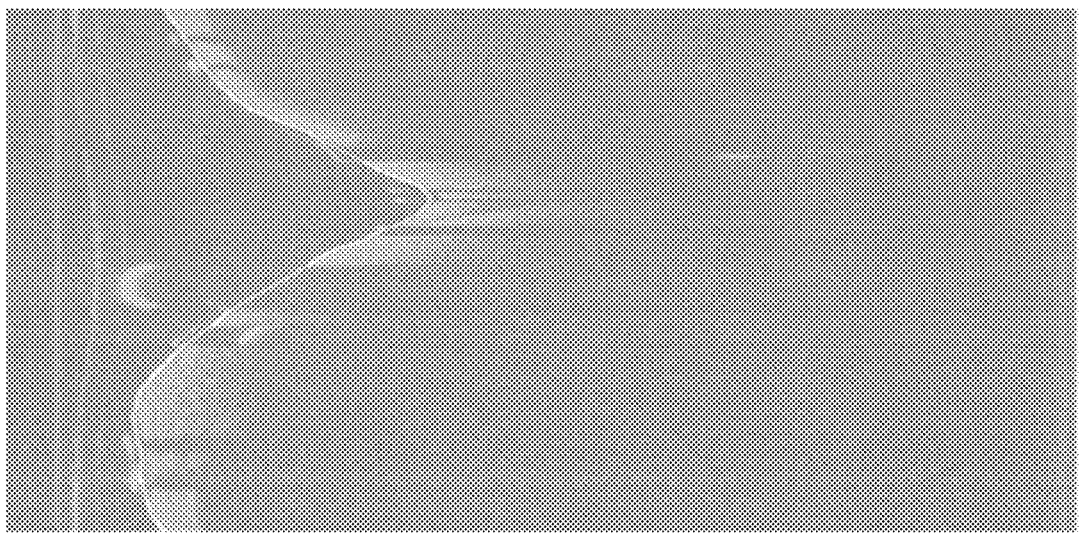

One or more embodiments of a method(s) for detecting lumen and artifacts may be performed with or without the filtering of the lumen edge (e.g., step 307 and/or step 308 of FIG. 3A may be removed as shown in FIG. 3B). For example, median filtering and/or low pass filtering the lumen edge is optional in one or more embodiments. In one or more embodiments, alternative methods for smoothing the lumen edge may be used in place of the median filtering and/or low pass filtering of the lumen edge.

One or more alternative embodiments of a method(s) for detecting lumen and artifacts may be performed by detecting a signal edge pixel from each one dimensional data (A-line). A-lines with a significant pulse peak may be selected. Each one dimensional data (A-line) may have its own detection threshold for pulse detection, and the respective threshold may change among different A-lines in an image. A gradient of one dimensional data (A-line) may be used to further determine the lumen edge pixel location.

One or more alternative embodiments of a method(s) for detecting lumen and artifacts may be performed by introducing an FRGR to distinguish the edges of the target or object (e.g., soft tissue), guide wire(s), stent(s) and/or any other component being used in the procedure. The pulse size of the one dimension data is introduced to distinguish the target or object (e.g., soft tissue), guide wire(s), stent(s), and/or any other component or artifact(s) related to the procedure(s).

One or more alternative embodiments of a method(s) for detecting lumen and artifacts may be performed by identifying the boundary region between the target or object (e.g., soft tissue) and the stent strut(s), guide wire(s) or other artifacts. Multiple peaks in an A-line may represent a blurred boundary between the target or object (e.g., soft tissue) and the stent strut(s), guide wire(s) or other artifacts. The multi-peaks may be used as a signature to identify the boundary.

One or more alternative embodiments of a method(s) for detecting lumen and artifacts may be performed by identifying the boundary region between the target or object (e.g., soft tissue) and narrow stent strut(s). Variation of the gradient along the horizontal direction (across the A-lines) in the region behind the detected lumen edge may be utilized to improve the determination of the location of the artifact region.

One or more alternative embodiments of a method(s) for detecting lumen and artifacts may be performed by identifying ghost signal(s) produced from reflection of stent(s). A ghost signal may cause multiple peaks in an A-line signal. One way to handle this is to remove the area where the multiple pulses/peaks are detected.

As aforementioned for one or more embodiments of a method(s) for detecting lumen and artifacts, interpolation may be used to sample the data that is removed, and to form the lumen edge. The final edge may be smoothed or polished using filters as aforementioned.

A computer, such as the console or computer 1200, 1200', may perform any of the aforementioned steps (e.g., steps S300-S309 of FIG. 3A; steps S300-S306 and S309 of FIG. 3B; etc.) for any system being manufactured or used, including, but not limited to, system 100, system 100', system 100", system 100'", etc.

Figure 14:
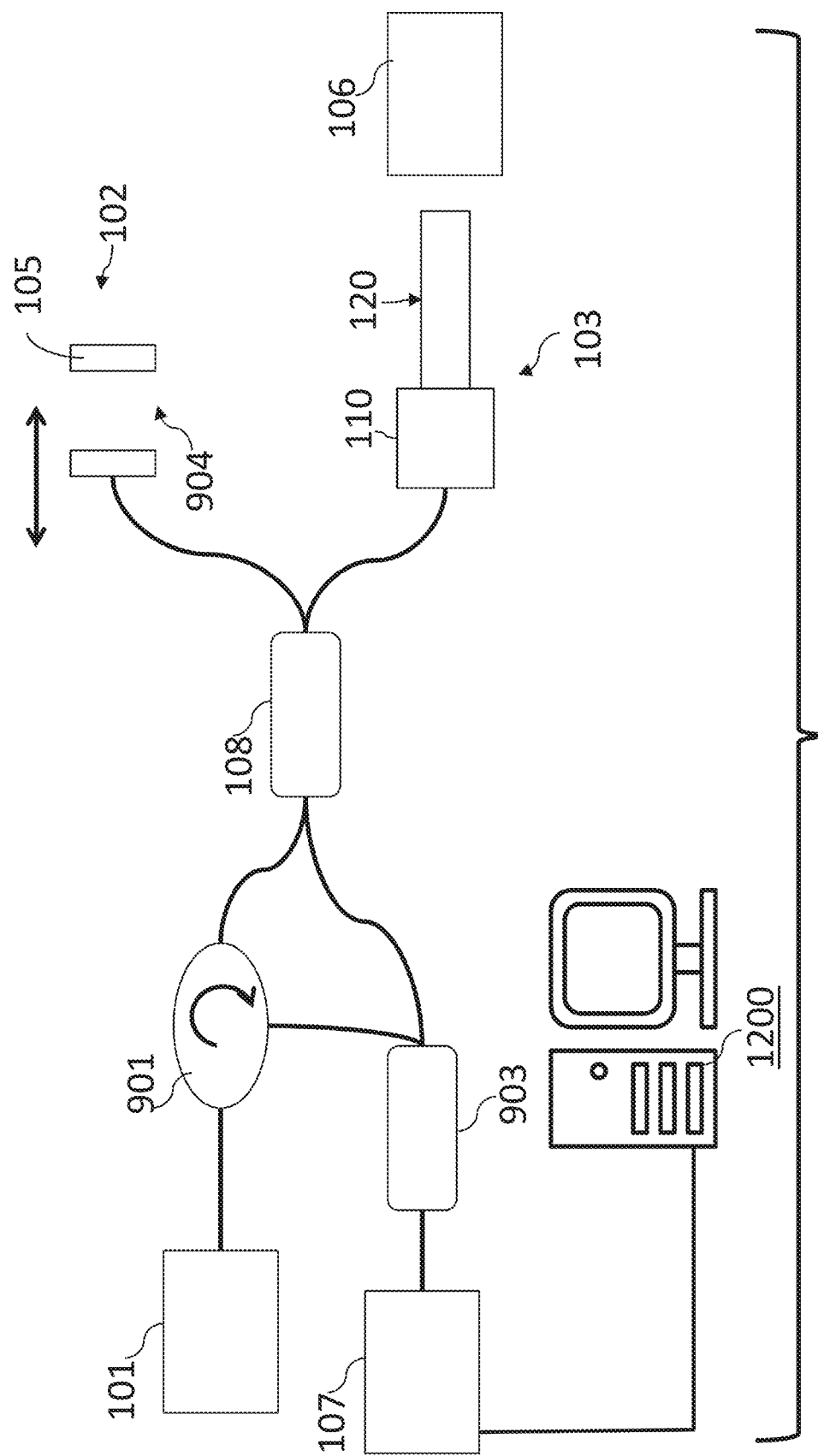
FIG. 14 is a diagram showing an embodiment of at least a second system which can utilize one or more lumen edges and artifacts detection techniques in accordance with one or more aspects of the present disclosure.

In accordance with one or more further aspects of the present disclosure, bench top systems may be utilized with the lumen edge and artifact(s) detection OCT techniques disclosed herein. FIG. 14 shows an example of a system that can utilize the lumen edge and artifact(s) detection OCT techniques for a bench-top such as for ophthalmic applications. A light from a light source 101 delivers and splits into a reference arm 102 and a sample arm 103 with a deflecting (or deflection) section 108. A reference beam goes through a length adjustment section 904 (which is optional in one or more embodiments) and is reflected from a reference mirror (such as reference mirror or reference reflection 105 shown in FIG. 1) in the reference arm 102 while a sample beam is reflected or scattered from a sample, target or object 106 in the sample arm 103 (e.g., via the PIU 110 and the catheter 120). In one embodiment, both beams combine at the deflecting/deflection section 108 and generate interference patterns. In one or more embodiments, the beams go to the combiner 903, and the combiner 903 combines both beams via the circulator 9010 and the deflecting section 108. The combined beams preferably are delivered to one or more detectors (such as the one or more detectors 107). The output of the beam splitter (see e.g., beam splitter 104 in FIG. 1), the deflecting section 108, and/or an interferometer is continuously acquired with one or more detectors, such as the one or more detectors 107. The electrical analog signals are converted to the digital signals to analyze them with a computer, such as, but not limited to, the computer 1200 (see FIG. 14; also shown in FIGS. 16-17 discussed further below), the computer 1200' (see e.g., FIG. 18 discussed further below), etc.

Figure 15:
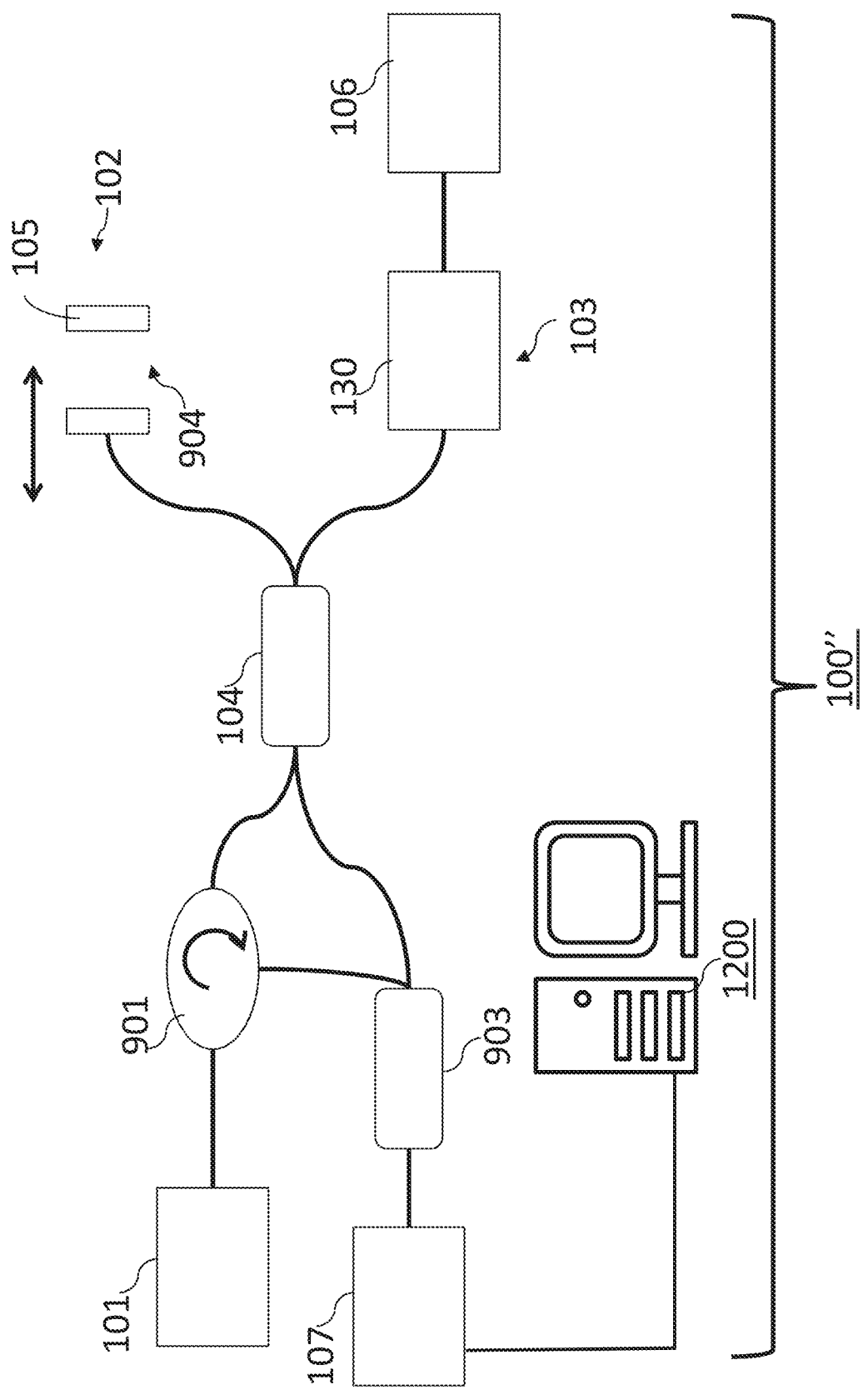
FIG. 15 is a diagram showing an embodiment of at least a third system which can utilize one or more lumen edges and artifacts detection techniques in accordance with one or more aspects of the present disclosure.

In one or more embodiments, the sample arm 103 may include a phase shift unit 103 for a bench top system(s) as shown in system 100" in FIG. 15. The sample 106 may be located at the place of the mirror 105 used with the phase shift unit 130 (e.g., as shown in FIG. 1). A light from a light source 101 delivers and splits into a reference arm 102 and a sample arm 103 with a splitter 104. A reference beam goes through a length adjustment section 904 and is reflected from a reference mirror (such as reference mirror 105 shown in FIG. 2) in the reference arm 102 while a sample beam is reflected or scattered from a sample, target and/or object 106 through a phase shift unit (such as the phase shift unit 130) in the sample arm 103. In one embodiment, both beams combine at the splitter 104 and generate interference patterns. In one or more embodiments, the beams go to the combiner 903, and the combiner 903 combines both beams via the circulator 901 and the splitter 104, and the combined beams are delivered to one or more detectors (such as the one or more detectors 107). The output of the beam splitter 104 and/or an interferometer is continuously acquired with one or more detectors, such as the one or more detectors 107. The electrical analog signals are converted to the digital signals to analyze them with a computer.

There are many ways to compute rotation, intensity, or any other measurement discussed herein, and/or to control and/or manufacture an MMOCT device/apparatus, system and/or storage medium, digital as well as analog. In at least one embodiment, a computer, such as the console or computer 1200, 1200', may be dedicated to control and/or use OCT devices, systems, methods and/or storage mediums for use therewith described herein.

Figure 16:
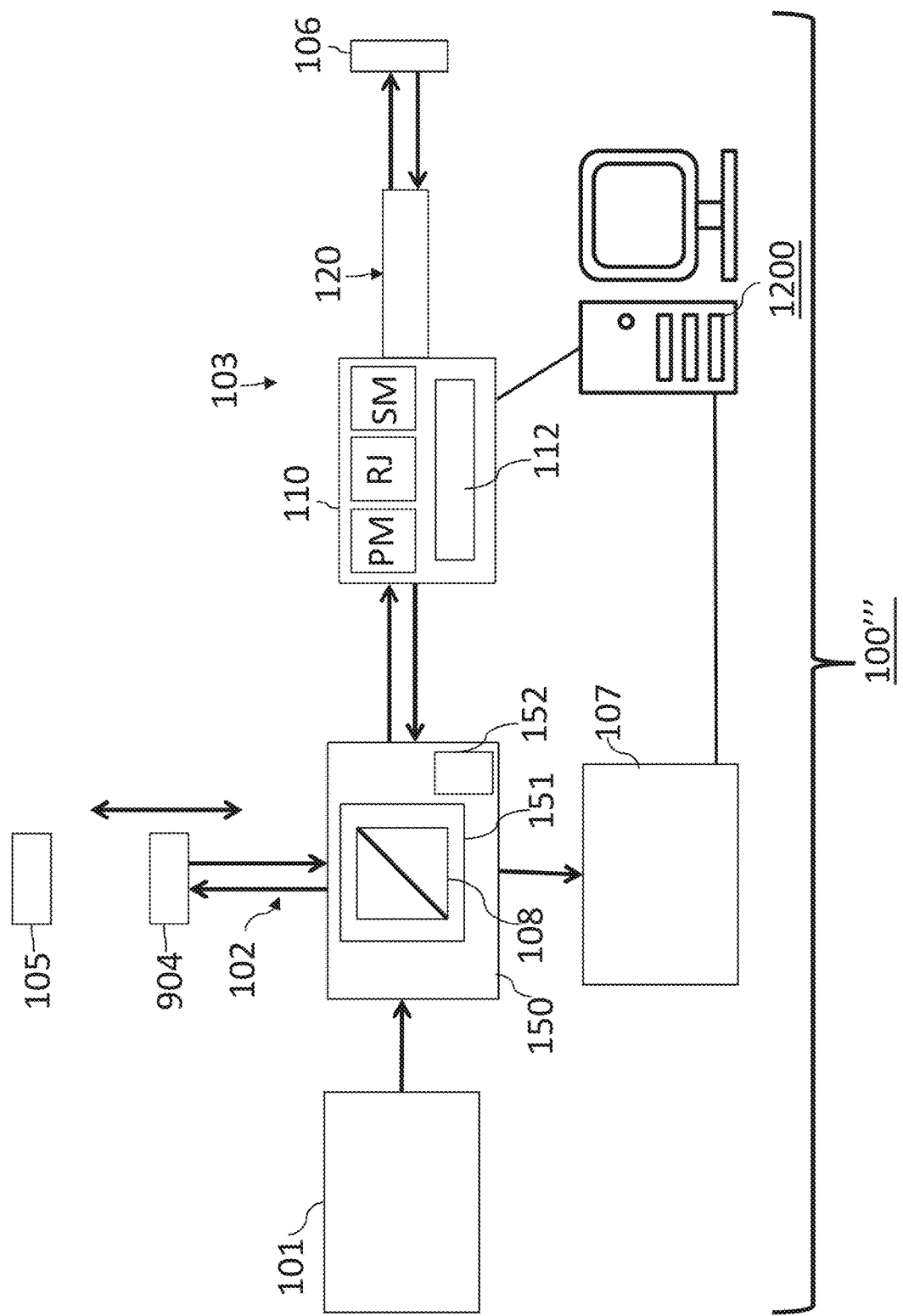
FIG. 16 is a diagram showing an embodiment of at least a fourth system which can utilize one or more lumen edges and artifacts detection techniques in accordance with one or more aspects of the present disclosure.

In accordance with one or more further aspects of the present disclosure, one or more other systems may be utilized with the lumen edge and artifact(s) detection OCT techniques disclosed herein. FIG. 16 shows an example of a system 100''' that may utilize the lumen edge and artifact(s) detection OCT techniques such as for ophthalmic applications. A light from a light source 101 delivers and splits into a reference arm 102 and a sample arm 103 with a deflecting section 108 (e.g., a beam splitter or other deflecting or deflected section discussed herein) located inside of an OCT imaging engine 1500, which may also include an OCT interferometer 151 (which may house or include the deflecting section 108) and a swept source engine 152 in one or more embodiments. A reference beam may pass through a length adjustment section 904, which may operate to change the distance of a reference mirror (such as reference mirror or reference reflection 105; also shown in FIG. 1) and is reflected from the reference reflection 105 in the reference arm 102 while a sample beam is reflected or scattered from a sample, target or object 106 in the sample arm 103. In one embodiment, both beams combine at the deflecting section 108 and generate interference patterns. In one or more embodiments, the combined beams are delivered to one or more detectors. The output of the interferometer 151 is continuously acquired with one or more detectors, such as the one or more detectors 107. The electrical analog signals are converted to the digital signals to analyze them with a computer, such as, but not limited to, the computer 1200 (see FIG. 16; also shown in FIG. 17 discussed further below), the computer 1200' (see e.g., FIG. 18 discussed further below), etc. In one or more embodiments, the sample arm 103 includes the PIU 110 and the catheter 120 so that the sample beam is reflected or scattered from the sample, target or object 106 as discussed herein. In one or more embodiments, the PIU 110 may include one or more motors to control the pullback operation of the catheter 120 (or one or more components thereof) and/or to control the rotation or spin of the catheter 120 (or one or more components thereof). For example, the PIU 110 may include a pullback motor (PM) and a spin motor (SM), and/or may include a motion control unit 112 that operates to perform the pullback and/or rotation features using the pullback motor PM and/or the spin motor SM. As discussed herein, the PIU 110 may include a rotary junction (e.g., rotary junction RJ as shown in FIG. 16). The rotary junction RJ may be connected to the spin motor SM so that the catheter 120 may obtain one or more views or images of the sample 106. The computer 1200 (or the computer 1200') may be used to control one or more of the pullback motor PM, the spin motor SM and/or the motion control unit 112. An OCT system may include one or more of the OCT engine 150, a computer (e.g., the computer 1200, the computer 1200', etc.), the PIU 110, the catheter 120, a monitor, etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

Unless otherwise discussed herein, like numerals indicate like elements. For example, while variations or differences exist between the systems, such as, but not limited to, the system 100, the system 100', the system 100", the system 100''', etc. (e.g., differences between the position(s) of the reference reflection 105 (and/or reference arm 102) depending on the OCT system or method being used), one or more features thereof may be the same or similar to each other, such as, but not limited to, the light source 101, the deflecting section 108 or other component(s) thereof (e.g., the console 1200, the console 1200', etc.). Those skilled in the art will appreciate that the light source 101, the at least one detector 107 and/or one or more other elements of the system 100, may operate in the same or similar fashion to those like-numbered elements of one or more other systems, such as, but not limited to, the system 100', the system 100", the system 100''', etc. as discussed herein. Those skilled in the art will appreciate that alternative embodiments of the system 100, the system 100', the system 100", the system 100''', and/or one or more like-numbered elements of one of such systems, while having other variations as discussed herein, may operate in the same or similar fashion to the like-numbered elements of any of the other systems (or component(s) thereof) discussed herein. Indeed, while certain differences exist between the system 100, the system 100', the system 100" and the system 100''', as discussed herein, there are similarities between the systems discussed herein. Likewise, while the console or computer 1200 may be used in one or more systems (e.g., the system 100, the system 100', the system 100", the system 100''', etc.), one or more other consoles or computers, such as the console or computer 1200', may be used additionally or alternatively.

There are many ways to compute power and/or detect lumen edge(s) and artifact(s), digital as well as analog. In at least one embodiment, a computer, such as the console or computer 1200, 1200', may be dedicated to the control and the monitoring of the OCT devices, systems, methods and/or storage mediums described herein.

The electric signals used for imaging may be sent to one or more processors, such as, but not limited to, a computer 1200 (see e.g., FIGS. 1, 14-16 and 17), a computer 1200' (see e.g., FIG. 18), etc. as discussed further below, via cable(s) or wire(s), such as, but not limited to, the cable(s) or wire(s) 113 (see FIG. 17).

Various components of a computer system 1200 (see e.g., the console or computer 1200 as shown in FIGS. 1, and 14-16) are provided in FIG. 17. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 17). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a FORJ or a device or system using same, such as, but not limited to, the system 100, the system 100', the system 100" and/or the system 100''', discussed herein above, via one or more lines 1213), and one or more other computer systems 1200 may include one or more combinations of the other aforementioned components. The CPU 1201 is configured to read and perform computer-executable instructions stored in a storage medium. The computer-executable instructions may include those for the performance of the methods and/or calculations described herein. The computer system 1200 may include one or more additional processors in addition to CPU 1201, and such processors, including the CPU 1201, may be used for controlling and/or manufacturing a device, system or storage medium for use with same or for use with any lumen detection and/or artifact(s) detection technique(s) discussed herein. The system 1200 may further include one or more processors connected via a network connection (e.g., via network 1206). The CPU 1201 and any additional processor being used by the system 1200 may be located in the same telecom network or in different telecom networks (e.g., performing, manufacturing, controlling and/or using technique(s) may be controlled remotely).

The I/O or communication interface 1205 provides communication interfaces to input and output devices, which may include the light source 101, a RJ, a PM, an SM, unit 150, unit 112, a microphone, a communication cable and a network (either wired or wireless), a keyboard 1210, a mouse (see e.g., the mouse 1211 as shown in FIG. 18), a touch screen or screen 1209, a light pen and so on. The Monitor interface or screen 1209 provides communication interfaces thereto.

Any methods and/or data of the present disclosure, such as the methods for using and/or manufacturing a device, system or storage medium for use with same and/or method(s) for detecting lumen edge(s) and/or artifact(s), including in OCT image(s), as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 18), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined, limited, or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, devices, systems, and computer-readable storage mediums related to the processors, such as, but not limited to, the processor of the aforementioned computer 1200, the processor of computer 1200', etc., as described above may be achieved utilizing suitable hardware, such as that illustrated in the figures. Functionality of one or more aspects of the present disclosure may be achieved utilizing suitable hardware, such as that illustrated in FIG. 17. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 17 or FIG. 18) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1200' is shown in FIG. 18. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 1200' includes a display 1209. The computer 1200' may connect with a rotary junction (e.g., RJ of FIG. 16, etc.), the motor PM, the motor SM, and/or one or more other components of a system (e.g., the system 100, the system 100', the system 100", the system 100''', etc.) via the operation interface 1214 or the network interface 1212. A computer, such as the computer 1200, 1200', may include the RJ, PM and/or the SM in one or more embodiments. The operation interface 1214 is connected with an operation unit such as a mouse device 1211, a keyboard 1210 or a touch panel device. The computer 1200' may include two or more of each component. Alternatively, the CPU 1201 or the GPU 1215 may be replaced by the field-programmable gate array (FPGA), the application-specific integrated circuit (ASIC) or other processing unit depending on the design of a computer, such as the computer 1200, the computer 1200', etc.

A computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 1200, 1200', communicates with the PIU 110, the rotary junction (e.g., the RJ, etc.), the motor PM, the motor SM, the catheter 120 and/or one or more other components of a system, such as the system 100, 100', 100", 100''', etc., to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate a system (e.g., the system 100, the system 100', the system 100", the system 100''', etc.), for example when performing OCT or other imaging technique, including, but not limited to, detection of lumen edge(s) and/or artifact(s). An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 100', the system 100", the system 100''', etc.) to set or change the imaging condition, and to start or end the imaging, and/or to start or end the lumen detection and/or artifact(s) detection. The laser source 101 of an OCT system as aforementioned may have interfaces to communicate with the computers 1200, 1200' to send and receive the status information and the control signals.

Similarly, the present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 7,872,759; 8,289,522; and 8,928,889 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942 and U.S. Patent Publication Nos. 2010/0092389, 2012/0101374, 2016/0228097, 2018/0045501 and 2018/0003481, each of which patents, patent publications and patent application(s) are incorporated by reference herein in their entireties.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

The invention claimed is:

1. An optical coherence tomography system for detecting one or more lumen edges and one or more artifacts in one or more images, the system comprising:

a light source that operates to produce a light;

an interference optical system that operates to: (i) receive and divide the light from the light source into a first light with which a target, object, or sample is to be irradiated and a second reference light, (ii) send the second reference light for reflection off of a reference mirror of the interference optical system, and (iii) generate interference light by causing reflected or scattered light of the first light with which the target, object, or sample has been irradiated and the reflected second reference light to combine or recombine, and to interfere, with each other, the interference light generating one or more interference patterns;

one or more detectors that operate to continuously acquire the interference light and/or the one or more interference patterns such that the one or more lumen edges and/or the one or more artifacts are detected in the one or more images, and the one or more artifacts are removed from the one or more images; and one or more processors that operate to:

filter two dimensional (2D) image data to smooth one or more images of the target, object, or sample;

compute vertical and horizontal gradients of the one or more filtered or smoothed images;

perform one dimensional (1D) filtering to smooth A-line data and gradients in each direction;

determine or detect a significant pulse for each filtered or smoothed A-line, and detect one or more lumen edge points in each filtered or smoothed A-line from the significant pulse; and form one or more complete lumen edges from the one or more filtered or smoothed images based on or using at least the significant pulse and/or at least the one or more detected lumen edge points such that the one or more artifacts are removed from the one or more filtered or smoothed images.

2. A method for detecting one or more lumen edges and one or more artifacts in one or more images, the method comprising:
filtering two dimensional (2D) image data to smooth one or more images of a target, object, or sample;
computing vertical and horizontal gradients of the one or more filtered or smoothed images;
performing one dimensional (1D) filtering to smooth A-line data and gradients in each direction;
determining or detecting a significant pulse for each filtered or smoothed A-line, and detecting one or more lumen edge points in each filtered or smoothed A-line from the significant pulse; and
forming one or more complete lumen edges from the one or more filtered or smoothed images based on or using at least the significant pulse and/or at least the one or more detected lumen edge points such that the one or more artifacts are detected and removed from the one or more filtered or smoothed images.

3. The method of claim 2, further comprising one or more of:
removing one or more edge points from a lumen edge of the one or more detected lumen edge points in accordance with at least one criterion;
removing one or more edge points from a lumen edge of the one or more detected lumen edge points corresponding to a predetermined falling and rising gradient ratio (FRGR) and predetermined-sized pulses;
removing one or more edge points from a lumen edge of the one or more detected lumen edge points corresponding to multi-peak pulses;
removing one or more edge points from a lumen edge of the one or more detected lumen edge points corresponding to multi-pulse A-lines;
removing one or more edge points from a lumen edge of the one or more detected lumen edge points, and marking one or more locations of the one or more removed edge points as a gap or gaps; and
removing one or more edge points from a lumen edge of the one or more detected lumen edge points, marking one or more locations of the one or more removed edge points as a gap or gaps, and filling any of the gap or gaps in the lumen edge and connecting remaining edge points to form the one or more complete lumen edges such that the one or more artifacts are removed from the one or more filtered or smoothed images.

4. The method of claim 3, wherein one or more of:
the filling step further comprises filling the gap or the gaps in the lumen edge using one or more of: linear interpolation, interpolation, and filtering;
the predetermined falling and rising gradient ratio (FRGR) comprises of a predetermined FRGR that is larger than a FRGR threshold;
the predetermined-size pulses are smaller than a pulse threshold;
the at least one criterion includes one or more of: a width criterion, and a criterion for an area under the pulse;
the significant pulse is determined or detected by applying the at least one criterion;
the at least one criterion is used to determine the significant pulse such that the at least one criterion produces the same or similar results compared with a different criterion of the at least one criterion; and
a multi-peak pulse is identified in a case where a falling edge of a peak rises again before the falling edge falls below the threshold.

5. The method of claim 3, wherein one or more of:
the removal of the one or more edge points from the lumen edge corresponding to the multi-pulse A-lines includes identifying and removing one or more ghost signals;
one or more ghost signals manifest as an additional pulse signal in the A-lines, which is used to identify the one or more ghost signals;
ghost signals are produced from one or more of: one or more reflections of the one or more artifacts, any signal or signals other than the signals from the target, object, or sample, and a luminance signal; and
in the event that ghost signals cause multiple peaks, the multiple peaks are removed to remove the ghost signals.

6. The method of claim 3, further comprising filtering the filled-in lumen edge to further smoothen the lumen edge, wherein the filtering of the filled-in lumen edge includes one or more of: lowpass filtering, Gaussian filtering, averaging filtering, and median filtering.

7. The method of claim 3, further comprising converting the lumen edge from polar to Cartesian coordinates.

8. The method of claim 2, wherein the imaging data is from optical coherence tomography (OCT), intravascular ultrasound (IVUS) or other lumen profile 2D polar image data.

9. The method of claim 2, wherein one dimensional data of each A-line and the respective gradient of each A-line are used to identify and determine an exact lumen edge pixel location.

10. The method of claim 2, wherein one or more of:
the filtering of the 2D image data includes one or more of: lowpass filtering, averaging filtering, median filtering, Gaussian filtering, and 2D lowpass Gaussian filtering;
the 1D filtering operates to smoothen the A-lines and the respective gradient along the A-lines; and
the filtering of the 2D image data operates to smooth out inter A-line noise as well as some of the intra A-line noise in order to reduce and/or remove the overall noise in the one or more filtered or smoothed images.

11. The method of claim 2, wherein the computing of vertical and horizontal gradients of the one or more filtered or smoothed images further comprises:
calculating the vertical gradients of the one or more filtered or smoothed images by applying a vertical convolution operation operator to the filtered or smoothed one or more images; and
calculating the horizontal gradients of the one or more filtered or smoothed images by applying a horizontal convolution operation operator to the filtered or smoothed one or more images.

12. The method of claim 11, wherein one or more of:
(i) the vertical convolution operation operator is one or more of a vertical Sobel operator and a vertical Prewitt operator, and the horizontal convolution operation operator is one or more of a horizontal Sobel operator and a horizontal Prewitt operator;

(ii) the vertical and horizontal Sobel operators are applied as the vertical and horizontal convolution operation operators as follows:

$$G_y = \begin{bmatrix} 1 & 4 & 6 & 4 & 1 \\ 2 & 8 & 12 & 8 & 2 \\ 0 & 0 & 0 & 0 & 0 \\ -2 & -8 & -12 & -8 & -2 \\ -1 & -4 & -6 & -4 & -1 \end{bmatrix} \otimes A, \text{ and}$$

$$G_x = \begin{bmatrix} -1 & -2 & 0 & 2 & 1 \\ -4 & -8 & 0 & 8 & 4 \\ -6 & -12 & 0 & 12 & 6 \\ -4 & -8 & 0 & 8 & 4 \\ -1 & -2 & 0 & 2 & 1 \end{bmatrix} \otimes A,$$

wherein A is the filtered or smoothed one or more images, $G_x$ and $G_y$ are the horizontal and vertical gradients, $\otimes$ denotes a two dimensional (2D) convolution operation, and each column in $G_y$ provides the gradient along an A-line while each row in $G_x$ provides the gradient across A-lines;

(iii) lower order Sobel operators are applied as the vertical and horizontal convolution operation operators as follows:

$$G_x = \begin{bmatrix} -1 & 0 & 1 \\ -2 & 0 & 2 \\ -1 & 0 & 1 \end{bmatrix} \otimes A, \text{ and}$$

$$G_y = \begin{bmatrix} 1 & 2 & 1 \\ 0 & 0 & 0 \\ -1 & -2 & -1 \end{bmatrix} \otimes A,$$

wherein A is the filtered or smoothed one or more images, $G_x$ and $G_y$ are the horizontal and vertical gradients, $\otimes$ denotes a two dimensional (2D) convolution operation, and each column in $G_y$ provides the gradient along an A-line while each row in $G_x$ provides the gradient across A-lines;

(iv) Prewitt operators are applied as the vertical and horizontal convolution operation operators as follows:

$$G_x = \begin{bmatrix} -1 & 0 & 1 \\ -1 & 0 & 1 \\ -1 & 0 & 1 \end{bmatrix} \otimes A, \text{ and}$$

$$G_y = \begin{bmatrix} 1 & 1 & 1 \\ 0 & 0 & 0 \\ -1 & -1 & -1 \end{bmatrix} \otimes A,$$

wherein A is the filtered or smoothed one or more images, $G_x$ and $G_y$ are the horizontal and vertical gradients, $\otimes$ denotes a two dimensional (2D) convolution operation, and each column in $G_y$ provides the gradient along an A-line while each row in $G_x$ provides the gradient across A-lines; and (v) the horizontal direction is across the A lines and the vertical direction is along an A line.

13. The method of claim 2, further comprising one or more of:
identifying a location of an edge pixel of each A-line by identifying a rising edge of the respective pulse to detect the edge pixel in each A-line such that 2D edge detection is converted into 1D pulse detection;
applying lowpass and highpass 1D filtering to the A-line signal(s) to remove a signal offset as well as to further smooth the A-line signal(s) for more reliable pulse detection;
applying a 1D filter to each corresponding or respective gradient of each A-line signal(s) for further smoothing;
avoiding a phase delay introduced by any filtering so that the pulse location is not shifted; and
independently processing each A-line by applying 1D highpass filtering to remove a background and by applying lowpass filtering to reduce noise.

14. The method of claim 2, wherein the determining or detecting the significant pulse for each filtered or smoothed A-line, and the detecting of the one or more lumen edge points in each filtered or smoothed A-line from the significant pulse step further comprises one or more of:
using an adaptive threshold or a determined threshold;
based on mean and maximum values of a filtered or smoothed A-line, computing a determined threshold as follows: Threshold=(mean+peak)/2, wherein the mean is an average of the filtered or smoothed A-line and the peak is the maximum value of the filtered or smoothed A-line;
based on maximum and minimum peak values of a filtered or smoothed A-line, computing a determined threshold as follows: Threshold=(min+peak)/2 where the peak is the maximum peak value of the filtered or smoothed A-line;
based on the maximum peak value of a filtered or smoothed A-line, computing a determined threshold as follows: Threshold=(Peak)×⅔, where the peak is the maximum peak value of the filtered or smoothed A-line; and
using an adaptive threshold or a determined threshold, wherein the adaptive threshold or the determined threshold is used to detect one or more of: (i) the significant pulse corresponding to a lumen edge in the specific A-line; and (ii) multi-peak pulses.

15. The method of claim 14, wherein:
any pulse above the adaptive threshold or the determined threshold is an edge pulse candidate;
the largest pulse among all of the edge pulse candidates defines the maximum peak or the significant pulse; and
the location of the highest peak of the 1D gradient signal along the A-line in the vicinity of the maximum peak is used to identify or detect the exact location of the one or more lumen edge points in the filtered or smoothed A-line.

16. The method of claim 15, further comprising one or more of:
placing together all of the one or more identified or detected lumen edge points from all the filtered or smoothed A-lines to form the one or more lumen edges for at least the target, object, or sample in the one or more filtered or smoothed images as a function of maximum peak locations versus A-line indices;
removing edge points and related boundary regions for any artifact or artifacts of the one or more artifacts in the one or more filtered or smoothed images from the one or more detected or identified lumen edge points; and removing edge points from the one or more lumen edges corresponding to one or more of: a predetermined falling and rising gradient ratio (FRGR), predetermined-sized pulses, a predetermined pulse width, and a predetermined area under the 1D signal pulse, wherein the predetermined FRGR, the predetermined-sized pulses, the predetermined pulse width, and the predetermined area under the 1D signal pulse correspond to a predetermined artifact or artifacts.

17. The method of claim 16, further comprising identifying artifact region locations us ng simple thresholding where the threshold is set as:

$$\text{Pulse Size Threshold} = \text{mean} - \text{sigma} * k1 \qquad (i)$$

or $$\text{FRGR Threshold} = \text{mean} + \text{sigma} * k2,$$

wherein mean and sigma are the mean and standard deviation of the corresponding signal, and k1 k2 are empirical parameters chosen between 1 to 2;

$$\text{Pulse Size Threshold} = \text{mean} + (\text{peak} - \text{mean})/3 \qquad (ii)$$

or $$\text{FRGR Threshold} = \text{mean} + (\text{peak} - \text{mean})/3,$$

wherein peak is a maximum value in A-line samples; or $$\text{Pulse Size Threshold} = \text{peak} - (\text{peak} - \text{mean})/2 \qquad (iii)$$

or $$\text{FRGR Threshold} = \text{peak} - (\text{peak} - \text{mean})/2.$$

18. The method of claim 2, further comprising one or more of:
using the horizontal gradients or a gradient variation along the horizontal direction to identify and remove the lumen edge data corresponding to a boundary region between soft tissue of the target, object, or sample in the filtered or smoothed one or more images and the one or more artifacts in the filtered or smoothed one or more images;
identifying one or more shadows in between a rising peak at one respective side and a falling edge at another respective side of each of the one or more shadows;
using the rising peak and the falling edge to remove a region of the one or more artifacts; and
using at least one threshold to identify a center location of the one or more artifacts.

19. The method of claim 2, wherein each one 1D data or A-line has its own detection threshold for pulse detection, and the respective threshold changes among different A-lines in the one or more images.

20. The method of claim 2, wherein one or more of:
the target, object, or sample is one or more of: tissue, soft tissue, a vessel, a biological tubular structure, an artery, an intestine, a vein, an organ, and a biological structure of a patient being imaged; and
the one or more artifacts includes one or more of: a stent, a stent strut, stents, stent struts, a guidewire, guidewires, and any tool or component used for an imaging procedure for the one or more images.

21. A non-transitory computer-readable storage medium storing at least one program that operates to cause one or more processors to execute a method for detecting one or more lumen edges and one or more artifacts in one or more images, the method comprising:
filtering two dimensional (2D) image data to smooth one or more images of a target, object, or sample;
computing vertical and horizontal gradients of the one or more filtered or smoothed images;
performing one dimensional (1D) filtering to smooth A-line data and gradients in each direction;
determining or detecting a significant pulse for each filtered or smoothed A-line, and detecting one or more lumen edge points in each filtered or smoothed A-line from the significant pulse; and
forming one or more complete lumen edges from the one or more filtered or smoothed images based on or using at least the significant pulse and/or based on or using at least the one or more detected lumen edge points such that the one or more artifacts are detected and removed from the one or more filtered or smoothed images.

* * * * *